United States Patent
Fix et al.

(10) Patent No.: US 11,120,258 B1
(45) Date of Patent: Sep. 14, 2021

(54) APPARATUSES, SYSTEMS, AND METHODS FOR SCANNING AN EYE VIA A FOLDING MIRROR

(71) Applicant: Facebook Technologies, LLC, Menlo Park, CA (US)

(72) Inventors: Alexander Jobe Fix, Seattle, WA (US); Andrew Wyman MacDonald, Seattle, WA (US); Dmitri Model, Fremont, CA (US); Mohammadhossein Daraeihajitooei, Seattle, WA (US); Javier San Agustin Lopez, Menlo Park, CA (US); Kirk Erik Burgess, Newark, CA (US); Mohamed Hegazy, Sammamish, WA (US); Thomas Scott Murdison, Kirkland, WA (US); Scott Robert Ramsby, Kirkland, WA (US); Sebastian Sztuk, Menlo Park, CA (US); Evan Gander, Seattle, WA (US)

(73) Assignee: Facebook Technologies, LLC, Menlo Park, CA (US)

( * ) Notice: Subject to any disclaimer, the term of this patent is extended or adjusted under 35 U.S.C. 154(b) by 243 days.

(21) Appl. No.: 16/515,063

(22) Filed: Jul. 18, 2019

(51) Int. Cl.
*A61B 3/14* (2006.01)
*G06K 9/00* (2006.01)
(Continued)

(52) U.S. Cl.
CPC ............ *G06K 9/00604* (2013.01); *A61B 3/10* (2013.01); *G06F 3/013* (2013.01); *G06F 3/16* (2013.01); *G06K 9/00597* (2013.01)

(58) Field of Classification Search
CPC ....................................................... A61B 3/14
See application file for complete search history.

(56) References Cited

U.S. PATENT DOCUMENTS 10,848,753 B1 * 11/2020 Cavin ................ G02B 27/0093
2012/0075168 A1 * 3/2012 Osterhout ............... G06F 3/011
345/8

(Continued)

OTHER PUBLICATIONS

Sigut et al., "Iris Center Corneal Reflection Method for Gaze Tracking Using Visible Light", IEEE Transactions on Biomedical Engineering, vol. 58, No. 2, Feb. 2011, pp. 441-419.

(Continued)

*Primary Examiner* — Olisa Anwah
(74) *Attorney, Agent, or Firm* — FisherBroyles, LLP

(57) ABSTRACT

A disclosed apparatus may include a line source configured to produce a line of light and a scanning device configured to scan the line of light across a scanning field in a scanning direction. The scanning field may include a receiving portion configured to receive an eye. The apparatus may also include a reflector positioned within the scanning field. During a primary period of a scan, the line of light may scan the receiving portion in a primary direction. During a secondary period of the scan, the reflector may reflect the line of light such that a reflection of the line of light scans the receiving portion in a secondary direction. The apparatus may also include a photodetector positioned to receive (1) an initial reflection during the primary period, and (2) a subsequent reflection during the secondary period. Various other methods, apparatuses, and computer-readable media are also disclosed.

20 Claims, 16 Drawing Sheets

(51) Int. Cl.
*G06F 3/16* (2006.01)
*G06F 3/01* (2006.01)
*A61B 3/10* (2006.01)

(56) References Cited

U.S. PATENT DOCUMENTS

| | | | | |
|---|---|---|---|---|
| 2012/0249797 | A1* | 10/2012 | Haddick | G06F 3/016 |
| | | | | 348/158 |
| 2017/0285343 | A1* | 10/2017 | Belenkii | H04N 9/3129 |
| 2018/0278924 | A1* | 9/2018 | Schowengerdt | G02B 27/0172 |
| 2018/0292654 | A1* | 10/2018 | Wall | G02B 27/0081 |
| 2018/0364485 | A1* | 12/2018 | Mallinson | G06F 3/012 |
| 2019/0004325 | A1* | 1/2019 | Connor | G02B 27/0172 |
| 2019/0050051 | A1* | 2/2019 | Cirucci | H04N 5/2256 |
| 2020/0150428 | A1* | 5/2020 | Greenberg | G02B 27/017 |
| 2020/0234408 | A1* | 7/2020 | Melakari | G06T 3/4053 |
| 2020/0285055 | A1* | 9/2020 | Shirko | G02B 30/56 |
| 2021/0109343 | A1* | 4/2021 | Gao | G02B 27/0081 |

OTHER PUBLICATIONS

Wikipedia, "Vertical-Cavity Surface-Emitting Laser", URL: https://en.wikipedia.org/w/index.php?title=Vertical-cavity_surface-emitting_laser&oldid=905438436, as accessed on Jul. 18, 2019, 7 pages.
Physorg, "New optical component set to revolutionise augmented reality", URL: https://phys.org/news/2014-07-optical-component-revolutionise-augmented-reality.html, Jul. 8, 2014, pp. 1-2.

* cited by examiner

APPARATUSES, SYSTEMS, AND METHODS FOR SCANNING AN EYE VIA A FOLDING MIRROR

BRIEF DESCRIPTION OF THE DRAWINGS

The accompanying drawings illustrate a number of exemplary embodiments and are a part of the specification. Together with the following description, these drawings demonstrate and explain various principles of the instant disclosure.

Figure 1:
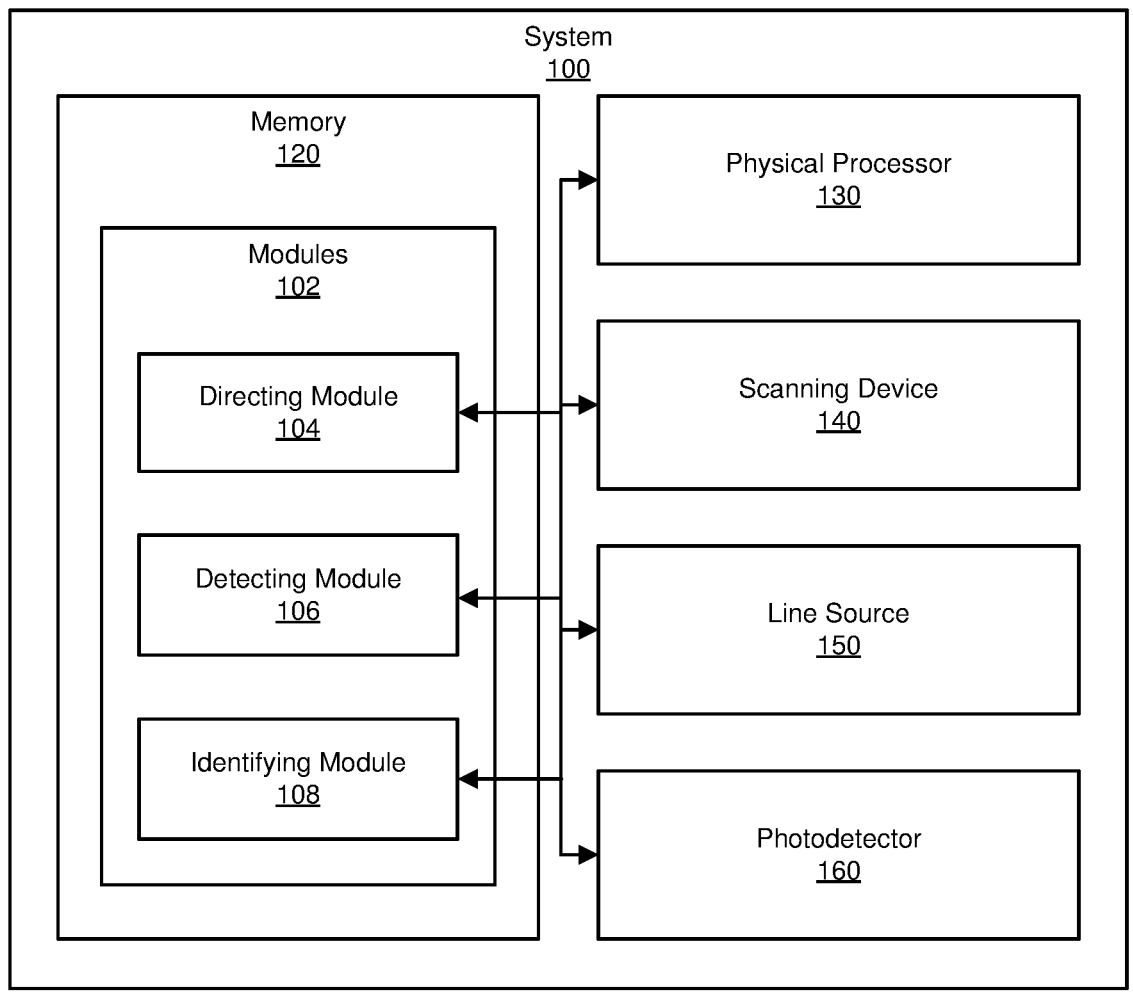
FIG. 1 is a block diagram of an example system for scanning an eye via a folding mirror.

Throughout the drawings, identical reference characters and descriptions indicate similar, but not necessarily identical, elements. While the exemplary embodiments described herein are susceptible to various modifications and alternative forms, specific embodiments have been shown by way of example in the drawings and will be described in detail herein. However, the exemplary embodiments described herein are not intended to be limited to the particular forms disclosed. Rather, the instant disclosure covers all modifications, equivalents, and alternatives falling within the scope of the appended claims.

DETAILED DESCRIPTION OF EXEMPLARY EMBODIMENTS

Putting on a virtual or augmented reality headset may be the beginning of a thrilling experience, one that may be more immersive than almost any other digital entertainment or simulation experience available today. Such headsets may enable users to travel through space and time, interact with friends in a three-dimensional world, or play video games in a radically redefined way. Virtual reality headsets may also be used for purposes other than recreation. Governments may use them for military training simulations, doctors may use them to practice surgery, and engineers may use them as visualization aids. Virtual reality and/or augmented reality headsets may also be used for productivity purposes. Information organization, collaboration, and privacy may all be enabled or enhanced through the use of virtual reality headsets.

Unfortunately, conventional virtual reality headsets may have some limitations. For example, conventional virtual reality headsets may be unable to track a gaze of a user, so as to identify an object within a real-world or virtual environment that the user may be looking at during a particular moment. This may reduce or inhibit immersiveness of some virtual reality experiences. Furthermore, conventional eye tracking solutions may, due to prohibitive power requirements, processing requirements, and so forth, be poorly adapted to incorporation within a conventional virtual reality headset. Hence, the present application identifies and addresses a need for eye tracking systems that may operate with lower power requirements and/or processing requirements than conventional eye tracking solutions.

The present disclosure is directed to apparatuses, systems, and methods for scanning a cornea via a folding mirror. As will be explained in greater detail below, embodiments of the instant disclosure may direct a scanning device to scan of a line of light, produced by a line source, across a scanning field in a scanning direction (e.g., from left to right, clockwise or counterclockwise about a point of rotation, etc.). In some examples, the scanning field may include a receiving portion configured to receive an eye of a user.

During a primary period of the scan, the line of light may scan the receiving portion in a primary direction. During a secondary period of the scan, a reflector positioned within the scanning field may reflect (e.g., fold an optical path of) the line of light such that a reflection of the line of light scans the receiving portion in a secondary direction (e.g., from right to left).

An example embodiment of this disclosure may also detect, via a photodetector, an initial reflection (e.g., a reflection of the line of light off of a tear-air interface of the cornea) produced by the line of light during the primary period and a subsequent reflection produced by the reflection of the line of light during the secondary period. An example embodiment may further identify a location on the eye based on at least one of the initial reflection and the subsequent reflection.

In some examples, the apparatuses, systems, and methods described herein may enable multiple orthogonal sweeps of a cornea during a single scan or sweep of a line source across a field in a single direction. Hence, embodiments of the apparatuses, systems, and methods described herein may efficiently perform two-dimensional scans of the cornea, which may enable identification and/or tracking of specific points on the cornea, tracking of a motion of the cornea, identification of a gaze direction of the eye, and so forth, with improved efficiency in comparison to conventional corneal scanning solutions that may require multiple scans of the cornea.

Furthermore, in some examples, the apparatuses, systems, and methods described herein may generate sparse signals associated with detected reflections, such that data representative of detected reflections may be sparse and easily processed by comparatively low power computing devices such as mobile or embedded computing devices. Hence, the apparatuses, systems, and methods described herein may reduce power consumption associated with conventional corneal scanning eye tracking systems and may reduce computing requirements associated with conventional eye tracking systems.

The following will provide, with reference to FIGS. 1, 2A-2B, and 4-15, detailed descriptions of apparatuses and systems for scanning an eye via a folding mirror. Detailed descriptions of corresponding computer-implemented methods will also be provided in connection with FIG. 3.

Note that various examples and illustrations provided herein may include one or more optical diagrams that may show one or more relationships among one or more rays of light and/or one or more reflective surfaces (e.g., FIGS. 4-8, 10-11 etc.). Such optical diagrams are intended to illustrate the principles described herein, but may not necessarily show particular, specific, or ideal positions of elements of one or more embodiments of the apparatuses, systems, and methods disclosed herein.

FIG. 1 is a block diagram of an example system 100 for scanning an eye via a folding mirror. As illustrated in this figure, example system 100 may include one or more modules 102 for performing one or more tasks. As will be explained in greater detail below, modules 102 may include a directing module 104 that directs a scanning device (e.g., scanning device 140) scan of a line of light, produced by a line source (e.g., line source 150), across a field in a scanning direction. In some examples, the scanning field may include a receiving portion configured to receive an eye of a user. During a primary period of the scan, the line of light may scan the receiving portion in a primary direction. Additionally, during a secondary period of the scan, a reflector positioned within the scanning field may reflect the line of light such that a reflection of the line of light scans the receiving portion in a secondary direction.

As further illustrated in FIG. 1, example system 100 may additionally include a detecting module 106 that may detect, via a photodetector (e.g., photodetector 160), an initial reflection produced by the line of light during the primary period of the scan and a subsequent reflection produced by the reflection of the line of light during the secondary period of the scan. Furthermore, example system 100 may also include an identifying module 108 that may identify a location on the eye based on at least one of the initial reflection and the subsequent reflection.

As further illustrated in FIG. 1, example system 100 may also include one or more memory devices, such as memory 120. Memory 120 generally represents any type or form of volatile or non-volatile storage device or medium capable of storing data and/or computer-readable instructions. In one example, memory 120 may store, load, and/or maintain one or more of modules 102. Examples of memory 120 include, without limitation, Random Access Memory (RAM), Read Only Memory (ROM), flash memory, Hard Disk Drives (HDDs), Solid-State Drives (SSDs), optical disk drives, caches, variations or combinations of one or more of the same, or any other suitable storage memory.

As further illustrated in FIG. 1, example system 100 may also include one or more physical processors, such as physical processor 130. Physical processor 130 generally represents any type or form of hardware-implemented processing unit capable of interpreting and/or executing computer-readable instructions. In one example, physical processor 130 may access and/or modify one or more of modules 102 stored in memory 120. Additionally or alternatively, physical processor 130 may execute one or more of modules 102 to facilitate scanning an eye via a folding mirror. Examples of physical processor 130 may include, without limitation, microprocessors, microcontrollers, central processing units (CPUs), Field-Programmable Gate Arrays (FPGAs) that implement softcore processors, Application-Specific Integrated Circuits (ASICs), portions of one or more of the same, variations or combinations of one or more of the same, or any other suitable physical processor.

Additionally, example system 100 may also include a scanning device 140. scanning device 140 may include any element that may scan a line of light across a field in a primary direction. For example, scanning device 140 may include a microelectromechanical system (MEMS) that may include one or more scanning micromirrors. The one or more micromirrors may reflect a line of light produced by a line source (e.g., line source 150) such that the line of light may scan across a field in the primary direction. Scanning device 140 may scan the line of light across the field in the primary direction—and may return the line of light to a starting point—at any suitable rate, such as 1 Hz, 10 Hz, 100 Hz, 1 kHz, 10 kHz, 100 kHz, 1 MHz, and so forth.

As also shown in FIG. 1, example system 100 may also include a line source 150. In some examples, a "line source" may include any illumination source that may project light across a surface in accordance with a predetermined shape. In some examples, line source 150 may generate a straight, narrow band of light that may be projected against and may extend across a surface. In some examples, the line source may generate a projection of a line that may have an aspect ratio greater than a threshold aspect ratio, such as 5:1, 10:1, 100:1, and so forth. In other words, in some examples, a projection of a line may have a substantially larger dimension along a first axis than along a second axis and, hence, may approximate a one-dimensional line segment when projected against and/or across a two- or three-dimensional surface.

For example, in some embodiments, line source 150 may include an infrared line source, such as an infrared laser source. In some additional examples, line source 150 may include a vertical-cavity surface-emitting laser (VCSEL) configured to emit a laser beam within an infrared range of the electromagnetic spectrum. Furthermore, line source 150 may include one or more optical elements that may form a line projection from light emitted from the infrared laser source, and may direct the line projection onto a surface, such as scanning device 140, a cornea of a user, and so forth. In some examples, line source 150 may include a laser fan source that may form a fan from a laser light source.

As an example, line source 150 may include a diffraction element that may diffract light from the infrared laser source into a line shape. As an additional example, line source 150 may include one or more microelectromechanical systems (MEMS) that may include one or more scanning micromirrors. The scanning micromirrors may reflect light from the infrared laser source into a line shape and/or may project the line-shaped infrared light onto a surface (e.g., a scanning device, a cornea of a user, etc.).

In some examples, line source 150 and scanning device 140 may be separate devices. In additional examples, line source 150 and scanning device 140 may be combined into a single device. For example, line source 150 and scanning device 140 may share a MEMS that may include one or more scanning micromirrors that may both (1) reflect light from a laser source into a line shape and (2) may reflect the line of light such that the line of light scans across a scanning field in a primary direction.

In additional embodiments, as will be described in additional detail below in reference to FIG. 10, scanning device 140 may scan a line of light, produced by line source 150, across a scanning field via an optical pathway of a waveguide display.

In some examples, as further shown in FIG. 1, example system 100 may also include a photodetector 160. Photodetector 160 may be positioned to receive light reflected by a cornea of a user. Furthermore, photodetector 160 may be communicatively coupled via any suitable data channel to physical processor 130, line source 150, and/or scanning device 140. Photodetector 160 may include any suitable sensor of light and/or other electromagnetic radiation. For example, in some embodiments, photodetector 160 may include a light-emitting diode (LED) (e.g., a reverse-biased LED), a photoresistor, a photodiode, a phototransistor, an active-pixel sensor (APS), a charge-coupled device (CCD), combinations of one or more of the same, and so forth.

Figure 9:
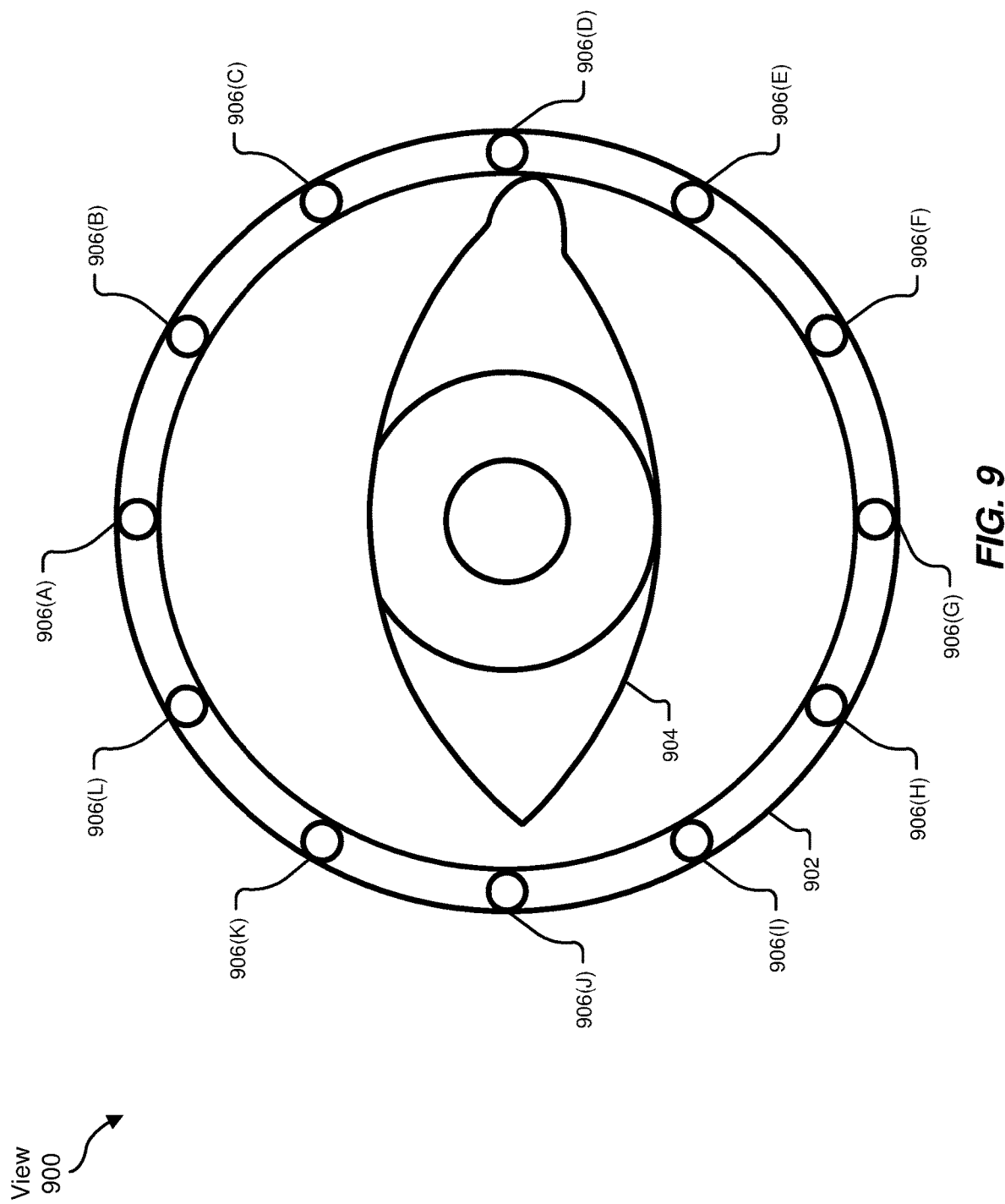
FIG. 9 is an illustration of an example photodetector in accordance with some embodiments described herein.

In some examples, as will be described in greater detail below in reference to FIG. 9, photodetector 160 may include a plurality of photosensitive elements, such as a number of LEDs, photodiodes, phototransistors, etc., arranged in a predetermined pattern relative to each other and/or relative to an eye of a user. Although some examples of photodetectors described herein may include a particular number of photosensitive elements, such examples are illustrative only and not intended to be limiting, as a photodetector may include any suitable number of photosensitive elements (e.g., at least one photosensitive element, at least four photosensitive elements, at least ten photosensitive elements, at least 100 photosensitive elements, etc.).

In some examples, photodetector 160 may include an event camera. In some examples, an "event" may include any change greater than a threshold value in one or more qualities of light (e.g., wavelength, brightness, radiance, polarity, luminance, illuminance, luminous intensity, luminous power, spectral exposure, etc.) received by a pixel included in an event camera during a predetermined period (e.g., 1 μs, 10 μs, 100 μs, 1000 μs, etc.). In some examples, an "event camera" may include any sensor that may asynchronously gather and transmit pixel-level data from one or more pixels in an image sensor array that may detect an event during a particular period of time (e.g., 1 μs, 10 μs, 100 μs, 1000 μs, etc.).

In additional or alternative embodiments, photodetector 160 may include a global-shutter camera. In some examples a "global-shutter camera" may include any imaging device that may scan an entire area of an image sensor (e.g., an array of photosensitive elements or pixels) simultaneously. In additional embodiments, photodetector 160 may include a rolling-shutter camera. In some examples, a "rolling-shutter camera" may include any imaging device that may scan an area of an image sensor (e.g., an array of photosensitive elements or pixels) line-by-line over a period of time (e.g., 60 Hz, 90 Hz, 120 Hz, etc.).

Although not shown in FIG. 1 or 2, in some embodiments, system 100 and/or system 200 may include an additional photodetector (e.g., an additional global shutter camera, an additional event camera, etc.). The additional photodetector may have additional or alternative properties and/or capabilities than photodetector 160, such as a higher or lower frame rate, a higher or lower resolution, employ a different photodetection method, and so forth. In some examples, one or more of the systems described herein may employ the additional photodetector to provide a higher or lower frequency update than photodetector 160.

Although not shown in FIG. 1, in some embodiments, example system 100 may also include a head-mounted display. In some examples, as will be described in greater detail below, a "head-mounted display" may include any type or form of display device or system that may be worn on or about a user's head and that may display visual content to the user. Head-mounted displays may display content in any suitable manner, including via a display screen (e.g., an LCD or LED screen), a projector, a cathode ray tube, an optical mixer, a waveguide display, etc. Head-mounted displays may display content in one or more of various media formats. For example, a head-mounted display may display video, photos, and/or computer-generated imagery (CGI).

Head-mounted displays may provide diverse and distinctive user experiences. Some head-mounted displays may provide virtual-reality experiences (i.e., they may display computer-generated or pre-recorded content), while other head-mounted displays may provide real-world experiences (i.e., they may display live imagery from the physical world). Head-mounted displays may also provide any mixture of live and virtual content. For example, virtual content may be projected onto the physical world (e.g., via optical or video see-through), which may result in augmented reality or mixed reality experiences. Head-mounted displays may be configured to be mounted to a user's head in a number of ways. Some head-mounted displays may be incorporated into glasses or visors. Other head-mounted displays may be incorporated into helmets, hats, or other headwear. Various examples of artificial reality systems that may include one or more head-mounted displays may be described in additional detail below in reference to FIGS. 13-15.

In some examples, scanning device 140 may be positioned to scan a line of light, produced by line source 150, across a field, that may include a cornea of a user, in a primary direction. Similarly, photodetector 160 may be positioned to receive light reflected by a cornea of a user. Additionally, in some examples, line source 150, scanning device 140, and/or photodetector 160 may be separate and distinct from a head-mounted display. In additional or alternative examples, line source 150, scanning device 140, and/or photodetector 160 may be included in (e.g., integrated within, positioned within, physically coupled to, etc.) a head-mounted display.

Furthermore, each element of example system 100 (e.g., memory 120, physical processor 130, line source 150, scanning device 140, and/or photodetector 160) may be communicatively coupled via any suitable data channel to other elements of example system 100. For example, as shown in FIG. 1, each of memory 120, line source 150, scanning device 140, and photodetector 160 may be in communication with physical processor 130. In this way, physical processor 130 may send and/or receive instructions and/or data from and/or to any other component of example system 100.

Figure 2A:
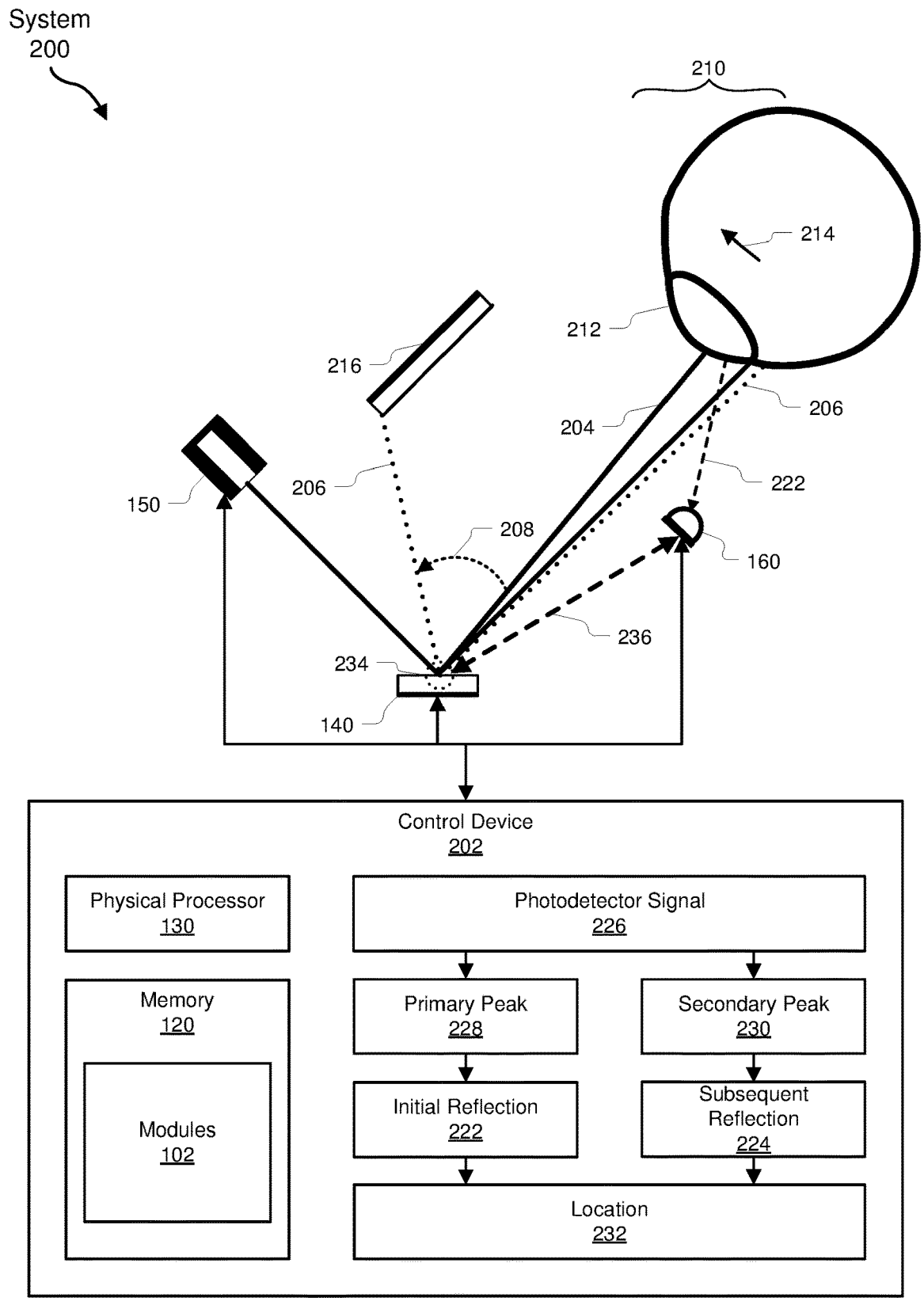
FIGS. 2A-2B are block diagrams of an example implementation of a system for scanning an eye via a folding mirror.
Figure 2B:
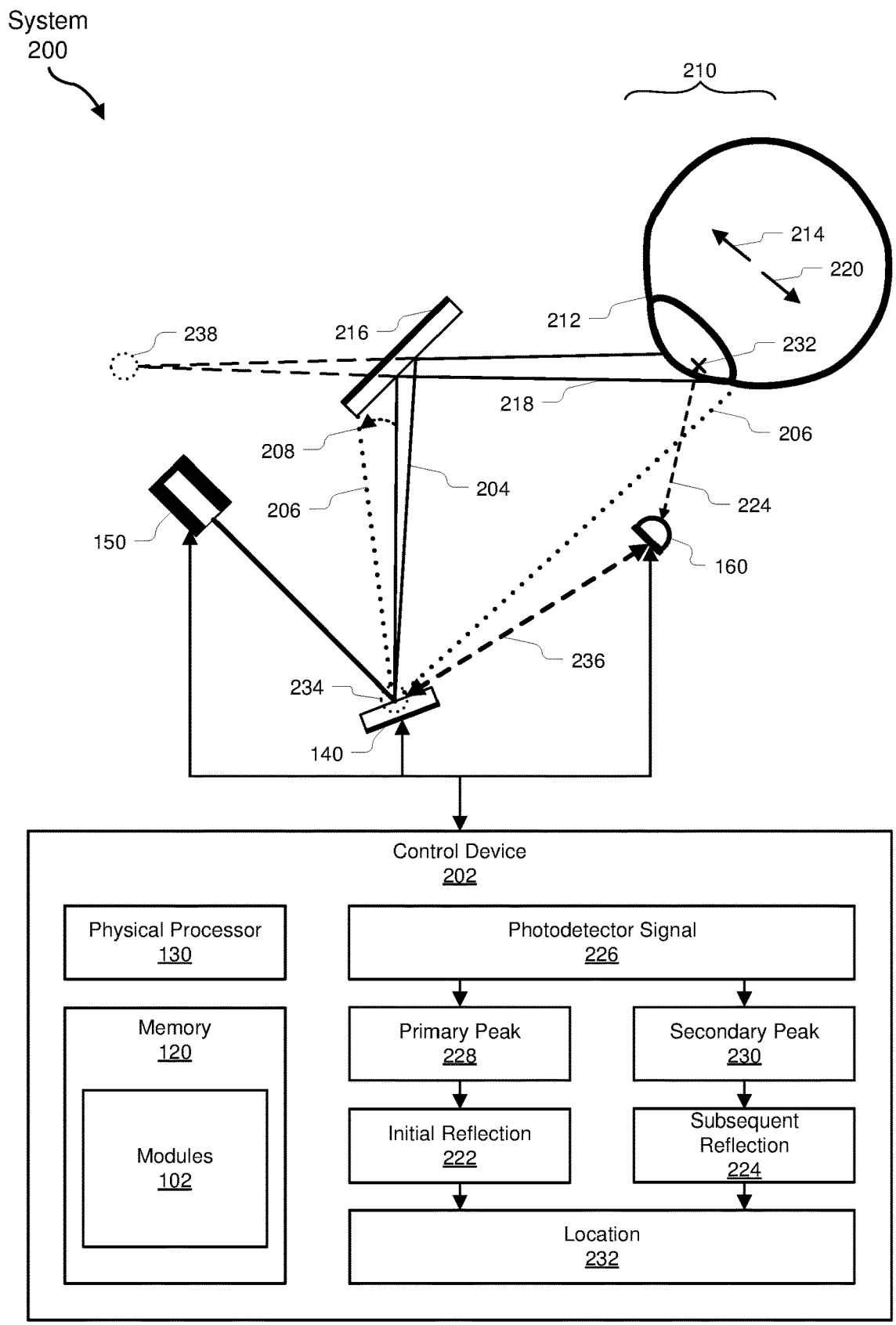

Example system 100 in FIG. 1 may be implemented in a variety of ways. For example, all or a portion of example system 100 may represent portions of an example system 200 ("system 200") in FIGS. 2A and 2B (collectively, FIG. 2). As shown in FIG. 2, system 200 may include a control device 202. In at least one example, control device 202 may be programmed with one or more of modules 102.

In at least one embodiment, one or more modules 102 from FIG. 1 may, when executed by control device 202, enable control device 202 to perform one or more operations to scan a cornea via a folding mirror. For example, as will be described in greater detail below, directing module 104 may cause control device 202 to direct a scanning device (e.g., scanning device 140) to scan a line of light (e.g., line of light 204), produced by a line source (e.g., line source 150), across a scanning field (e.g., scanning field 206) in a scanning direction (e.g., scanning direction 208).

In some examples, the scanning field may include a receiving portion (e.g., receiving portion 210) configured to receive an eye of a user (e.g., eye 212). During a primary period of the scan, the line of light may scan the receiving portion in a primary direction (e.g., primary direction 214). During a secondary period of the scan, a reflector (e.g., reflector 216) positioned within the scanning field may reflect the line of light such that a reflection of the line of light (e.g., reflection 218) may scan the receiving portion in a secondary direction (e.g., secondary direction 220).

Additionally, detecting module 106 may cause control device 202 to detect, via a photodetector (e.g., photodetector 160), an initial reflection (e.g., initial reflection 222) produced by the line of light during the primary period of the scan and a subsequent reflection (e.g., subsequent reflection 224) produced by the reflection of the line of light during the secondary period of the scan. In some examples, detecting module 106 may detect the initial reflection by determining a time of a primary peak in a signal (e.g., photodetector signal 226) produced by the photodetector during the primary period (e.g., primary peak 228), and detecting module 106 may detect the subsequent reflection by determining a time of a secondary peak in the signal produced by the photodetector during the secondary period (e.g., secondary peak 230).

Furthermore, identifying module 108 may cause control device 202 to identify a location on the eye (e.g., location 232) based on at least one of the initial reflection and the subsequent reflection. In some examples, identifying module 108 may further cause control device 202 to track a motion of the cornea based on the initial reflection, the subsequent reflection, a point of rotation associated with the scanning device (e.g., point of rotation 234) and a position of the photodetector relative to the point of rotation (e.g., photodetector position 236). In additional examples, identifying module 108 may further cause control device 202 to determine an apparent point of rotation associated with the reflection of the line of light (e.g., apparent point of rotation 238). In further examples, tracking of the motion of the cornea may be further based on the apparent point of rotation associated with the reflection of the line of light.

Control device 202 generally represents any type or form of computing device capable of reading and/or executing computer-executable instructions. Examples of control device 202 include, without limitation, servers, desktops, laptops, tablets, cellular phones, (e.g., smartphones), personal digital assistants (PDAs), multimedia players, embedded systems, wearable devices (e.g., smart watches, smart glasses, etc.), gaming consoles, combinations of one or more of the same, or any other suitable computing device.

In at least one example, control device 202 may be a computing device programmed with one or more of modules 102. All or a portion of the functionality of modules 102 may be performed by control device 202 and/or any other suitable computing system. As will be described in greater detail below, one or more of modules 102 from FIG. 1 may, when executed by at least one processor of control device 202, may enable control device 202 to scan a cornea via a folding mirror.

Many other devices or subsystems may be connected to system 100 in FIG. 1 and/or system 200 in FIG. 2. Conversely, all of the components and devices illustrated in FIGS. 1 and 2 need not be present to practice the embodiments described and/or illustrated herein. The devices and subsystems referenced above may also be interconnected in different ways from those shown in FIG. 2. Systems 100 and 200 may also employ any number of software, firmware, and/or hardware configurations. For example, one or more of the example embodiments disclosed herein may be encoded as a computer program (also referred to as computer software, software applications, computer-readable instructions, and/or computer control logic) on a computer-readable medium.

Figure 3:
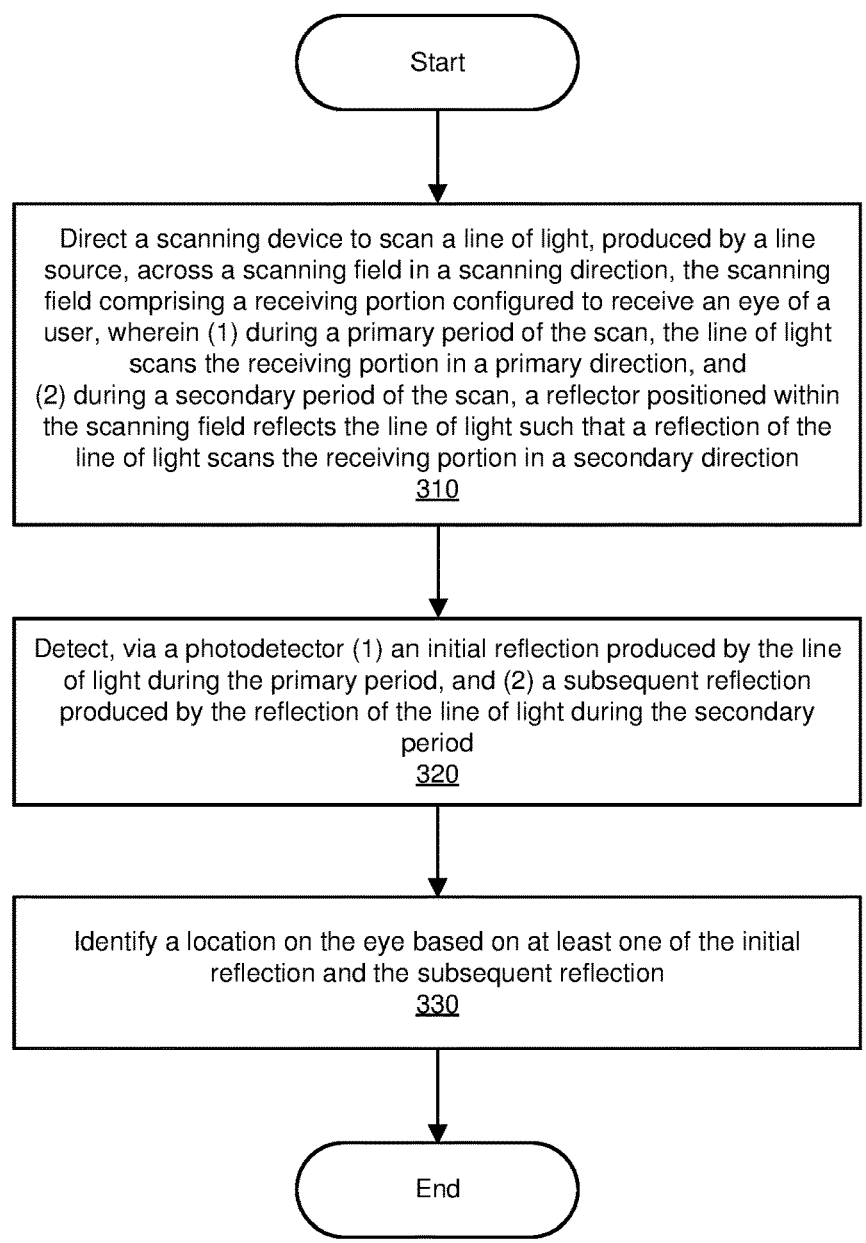
FIG. 3 is a flow diagram of an example method for scanning an eye via a folding mirror.

FIG. 3 is a flow diagram of an example computer-implemented method 300 for scanning an eye via a folding mirror. The steps shown in FIG. 3 may be performed by any suitable computer-executable code and/or computing system, including system 100 in FIG. 1, system 200 in FIG. 2, and/or variations or combinations of one or more of the same. In one example, each of the steps shown in FIG. 3 may represent an algorithm whose structure includes and/or is represented by multiple sub-steps, examples of which will be provided in greater detail below.

As illustrated in FIG. 3, at step 310, one or more of the systems described herein may direct a scanning device to scan of a line of light, produced by a line source, across a scanning field in a scanning direction. For example, directing module 104 may direct scanning device 140 to scan line of light 204 across scanning field 206 in scanning direction 208. In some examples, scanning field 206 may include receiving portion 210 configured to receive an eye of a user, such as eye 212. During a primary period of the scan, line of light 204 may scan across receiving portion 210 in a primary direction 214 and, during a secondary period of the scan, a reflector 216 may reflect line of light 204 such that a reflection 218 of line of light 204 may scan receiving portion 210 in a secondary direction 220.

By way of illustration, FIGS. 4-8 illustrate various views 400-800 of an eye of a user that includes an eye 212 during a scan of line of light 204 across scanning field 206 in scanning direction 208. Whereas FIGS. 2A and 2B may illustrate an overhead view of such a scan, FIGS. 4-8 may illustrate an alternate or frontal view of a similar scan. As shown in view 400 in FIG. 4, line source 150 may generate and/or scanning device 140 may direct line of light 204 toward an extreme portion of scanning field 206 (e.g., a left-hand side of scanning field 206). As noted above, in some examples, line source 150 may include a laser fan source, and line of light 204 may include an edge of a laser fan generated by line source 150 and directed toward and/or across scanning field 206 by scanning device 140.

Scanning device 140 may then begin to scan line of light 204 across scanning field 206 in scanning direction 208. As shown, scanning field 206 may include a receiving portion 210 that may be configured to receive eye 212. As scanning device 140 scans line of light 204 across receiving portion 210, line of light 204 may scan across eye 212 in primary direction 214.

Figure 5:
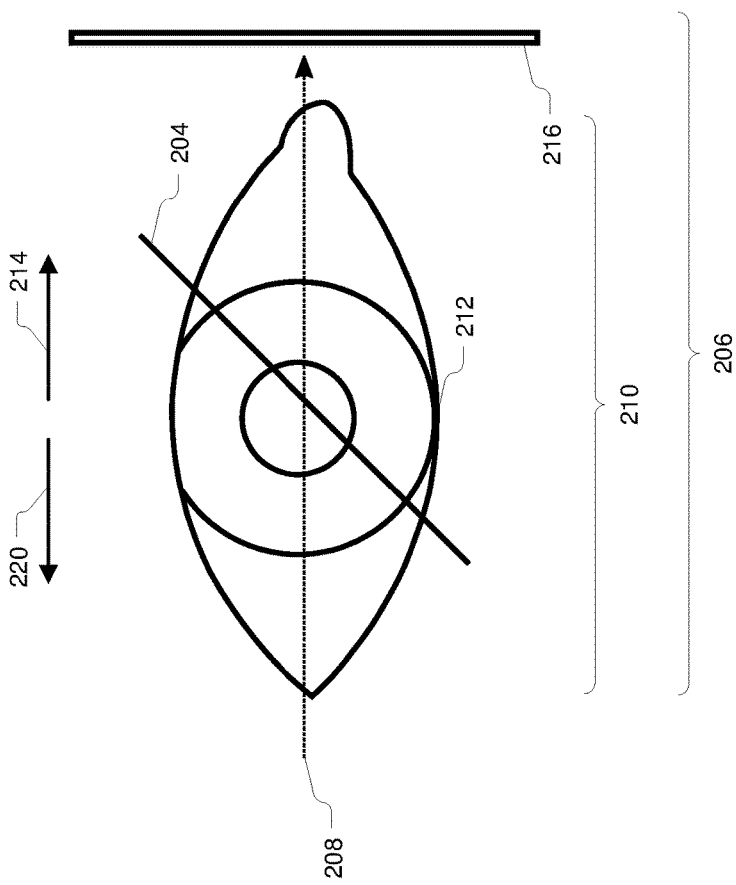
Figure 6:
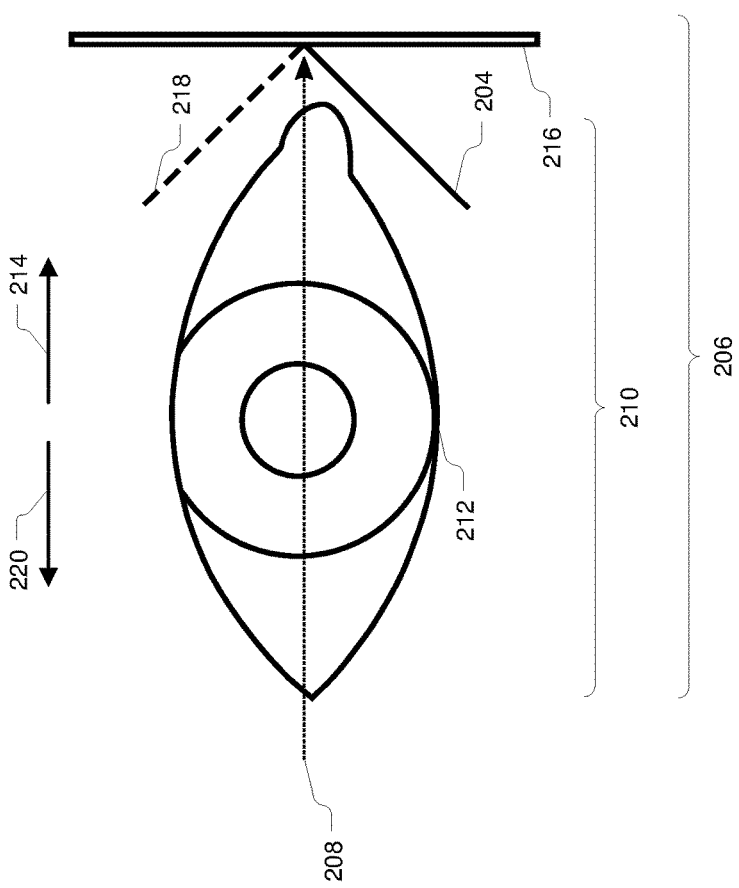

FIG. 5 includes a view 500 of the eye of the user during the scan of line of light 204 across scanning field 206 in scanning direction 208. As shown, scanning device 140 has caused line of light 204 to scan across approximately one-half of receiving portion 210 of scanning field 206 and eye 212. Continuing to FIG. 6, view 600 shows eye 212 during the scan of line of light 204 across scanning field 206 after the primary period of the scan has completed and scanning device 140 has completed a scan across receiving portion 210 of scanning field 206. In FIG. 6, the secondary period of the scan has begun and scanning device 140 has begun to scan line of light 204 across reflector 216. Line of light 204 has intersected with reflector 216, and reflector 216 has begun to reflect line of light 204 such that reflection 218 has begun to scan across receiving portion 210 (and therefore eye 212) in secondary direction 220.

Figure 7:
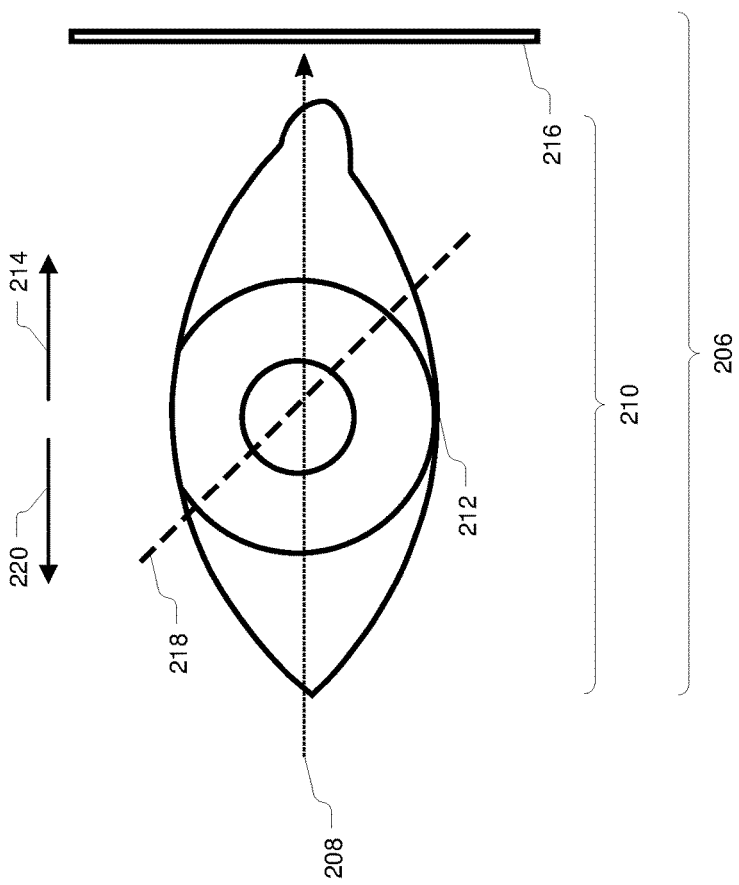

Continuing to FIG. 7, view 700 shows a continuation of the secondary period of the scan of the line of light 204 across scanning field 206 in scanning direction 208. As line of light 204 (not shown in FIG. 7) has continued to scan across reflector 216, reflector 216 has continued to reflect line of light 204 such that reflection 218 has continued to scan across eye 212 in secondary direction 220. As shown, reflection 218 of line of light 204 has reached a point approximately one-half of the way across eye 212.

Figure 8:
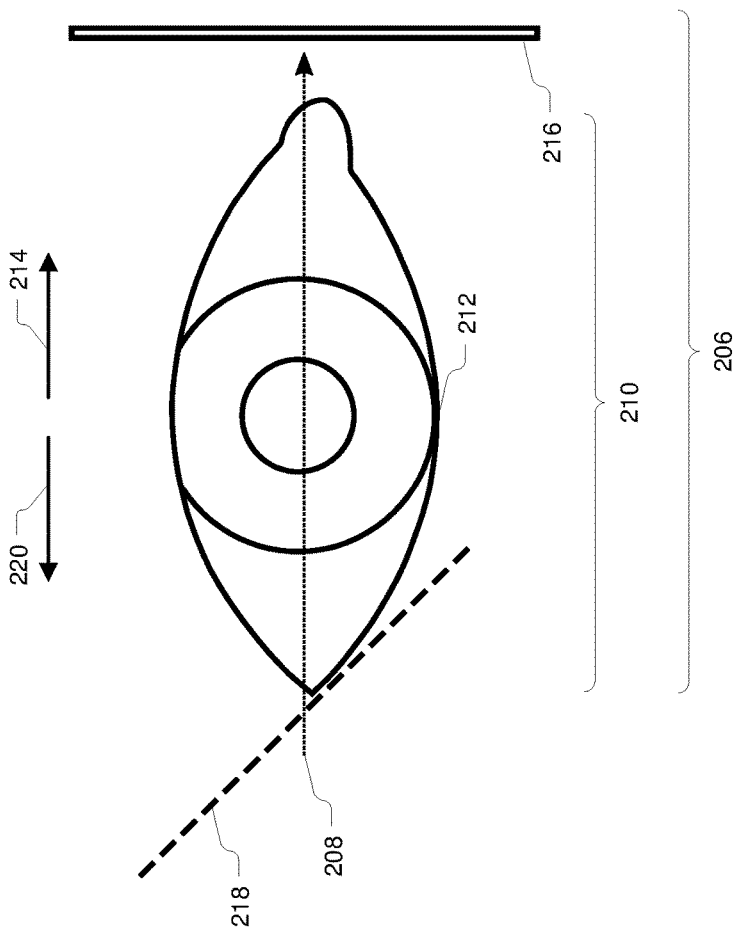

In FIG. 8, view 800 shows a further continuation of the secondary period of the scan of the line of light 204 across scanning field 206 in scanning direction 208. As line of light 204 (not shown in FIG. 8) has continued to scan across reflector 216, reflector 216 has continued to reflect line of light 204 such that reflection 218 has continued to scan across eye 212 in secondary direction 220. As shown, reflection 218 of line of light 204 has completed a scan of eye 212 in secondary direction 220.

In some examples, as shown in FIGS. 4-8, line of light 204 may be oriented in a primary orientation relative to primary direction 214 (e.g., relative to a line defined by a motion of line of light 204 across eye 212 in primary direction 214) and reflection 218 may be oriented in a secondary orientation relative to primary direction 214 (e.g., relative to the line defined by the motion of line of light 204 across eye 212 in primary direction 214).

Figure 4:
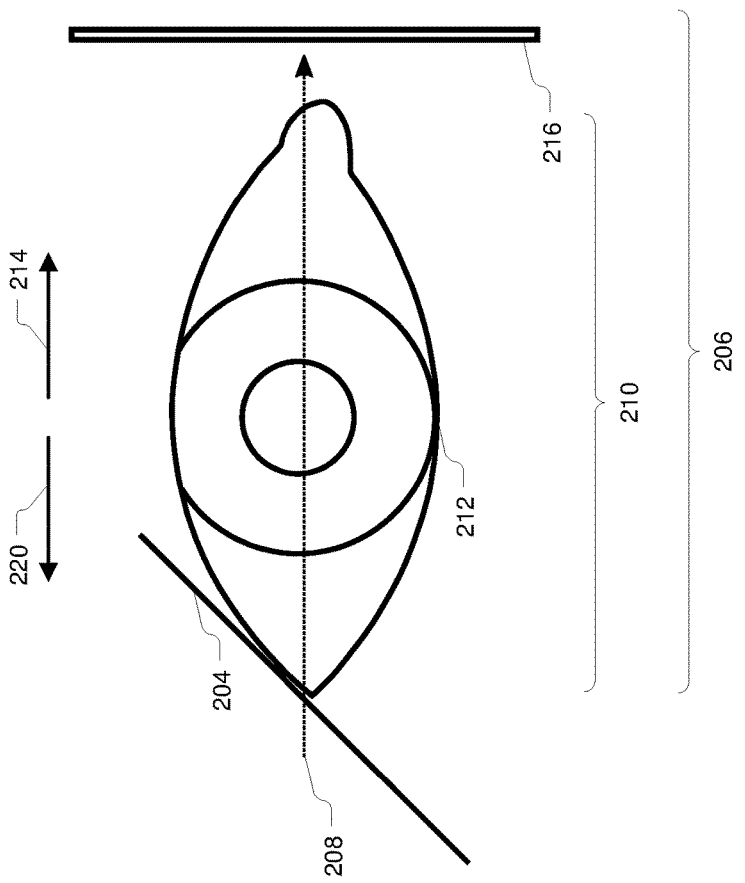
FIGS. 4-8 illustrate a scan of a scanning field that includes (1) a receiving portion configured to receive an eye of a user and (2) a reflector in accordance with some embodiments described herein.

The primary orientation of line of light 204 may be any suitable angle and the secondary orientation of reflection 218 may be any suitable angle. For example, as shown in FIG. 4, line of light 204 may be canted at an angle of approximately 45° relative to primary direction 214. Likewise, in some examples, reflection 218 may be oriented in a secondary orientation relative to primary direction 214. For example, as shown in FIG. 7, reflection 218 may be canted at an angle of approximately 135° relative to primary direction 214. In some examples, as shown in FIGS. 4-8, the primary orientation may be orthogonal in a common plane to the secondary orientation. As will be described in greater detail below, by orienting line of light 204 in a primary orientation and reflection 218 in a secondary orientation, the scan of eye 212 by line of light 204 and the scan of eye 212 by reflection 218 may enable identification of one or more points on eye 212 via a single, one-dimensional scan of line of light 204 across scanning field 206.

Directing module 104 may direct scanning device 140 to scan line of light 204 across scanning field 206 in scanning direction 208 in a variety of contexts. For example, directing module 104 may communicate any suitable activation instruction via any suitable communications medium to scanning device 140 that may instruct scanning device 140 to execute the scan in scanning direction 208. In additional or alternative embodiments, directing module 104 may also, in addition to directing scanning device 140 to execute the scan of line of light 204 across scanning field 206 in scanning direction 208, direct line source 150 to begin to produce line of light 204 that scanning device 140 may scan across scanning field 206.

In some examples, directing module 104 may direct scanning device 140 and/or line source 150 to scan line of light 204 in a predetermined and/or specific pattern. In some examples, such a pattern may be based on and/or correlated with an actual reflection received from an eye and/or an expected reflection from an eye. For example, as shown in FIGS. 4-8, directing module 104 may direct scanning device 140 and/or line source 150 to scan line of light 204 across receiving portion 210 in a substantially unidirectional or bidirectional fashion. In additional examples, directing module 104 may direct scanning device 140 and/or line source 150 to scan line of light 204 in an alternative pattern, such as a vertical direction across receiving portion 210, a multidimensional path across a portion of receiving portion 210, a radial path across receiving portion 210, and so forth.

In additional or alternative embodiments, directing module 104 may direct scanning device 140 and/or line source 150 to scan line of light 204 across receiving portion 210 in an adaptive manner. For example, directing module 104 may direct scanning device 140 and/or line source 150 to scan line of light 204 across a portion of receiving portion 210 such that light from line of light 204 may reflect from eye 212 where there may be a higher likelihood that one or more of the systems described herein may detect the light reflected from eye 212 (e.g., detecting module 106 via photodetector 160). Additionally or alternatively, directing module 104 may similarly direct scanning device 140 and/or line source 150 to scan line of light 204 across a portion of receiving portion 210 such that light from line of light 204 may not create reflections from and/or within one or more portions of receiving portion 210 (e.g., a sclera of eye 212). Such an adaptive scanning method may include and/or be based on one or more determined locations on eye 212, as will be described in greater detail below.

For example, one or more of the systems described herein (e.g., identifying module 108) may, as will be described in greater detail below, identify a location on an eye (e.g., location 232) based on at least one of an initial reflection (e.g., initial reflection 222) and a subsequent reflection (e.g., subsequent reflection 224). In a subsequent scan, directing module 104 may cause and/or line source 150 and/or scanning device 140 to Returning to FIG. 3, at step 320, one or more of the systems described herein may detect, via a photodetector, (1) an initial reflection produced by the line of light during the primary period, and (2) a subsequent reflection produced by the reflection of the line of light during the secondary period. For example, detecting module 106 may, as part of control device 202, cause control device 202 to detect, via photodetector 160, (1) initial reflection 222 produced by line of light 204 during the primary period, and (2) subsequent reflection 224 produced by reflection 218 during the secondary period.

In some examples, a reflection detected by photodetector 160 (e.g., initial reflection 222 and/or subsequent reflection 224) may include any reflection of light from a structure of an eye (e.g., a cornea of eye 212). In some examples, a reflection detected by photodetector 160 may include a glint. In some examples, a glint may include a reflection of an object (e.g., line of light 204 and/or reflection 218) from a structure of an eye. In some examples, a glint may include one or more Purkinje images, such as a first Purkinje image (P1) that may include a reflection from an outer surface of a cornea, a second Purkinje image (P2) that may include a reflection from an inner surface of the cornea, a third Purkinje image (P3) that may include a reflection from an outer (e.g., anterior) surface of a lens, and/or a fourth Purkinje image (P4) that may include a reflection from an inner (e.g., posterior) surface of the lens.

As described above, a "photodetector" (e.g., photodetector 160, photodetector 902, etc.) may include any suitable sensor of light and/or other electromagnetic radiation. FIG. 9 shows a view 900 of a photodetector 902 that may be included in one or more apparatuses and/or systems described herein. As shown, photodetector 902 may include a frame arranged and/or positioned to receive light reflected by a cornea of an eye 904 of a user. As described above in reference to photodetector 160, photodetector 902 may include a plurality of photosensitive elements 906 (e.g., photosensitive elements 906(A)-906(L)). Although photodetector 902 is shown in FIG. 9 as including twelve photosensitive elements 906, a photodetector (e.g., photodetector 160, photodetector 902, etc.) may include any suitable number of photosensitive elements (e.g., four photosensitive elements, twelve photosensitive elements, twenty photosensitive elements, etc.).

Each photosensitive element 906 may be configured and/or oriented to detect light originating from a line of light (e.g., line of light 204) and reflected from a cornea (e.g., eye 212) of eye 904. For example, each photosensitive element 906 may include an LED (e.g., a reverse-biased LED), a photoresistor, a photodiode, a phototransistor, an APS, a CCD, a combination of one or more of the same, and/or any other suitable photosensitive element. Furthermore, each photosensitive element 906 may be positioned at a predetermined position within photodetector 902 and/or may be configured to receive light reflected by a particular portion of the cornea and/or at particular angles from one or more particular portions of the cornea.

Detecting module 106 may detect, via a photodetector (e.g., photodetector 160, photodetector 902, etc.), initial reflection 222 during the primary period and subsequent reflection 224 during the secondary period in a variety of contexts. For example, detecting module 106 may detect initial reflection 222 by determining a time of a primary peak in a signal produced by a photodetector (e.g., primary peak 228 in photodetector signal 226) during a primary period of a scan of scanning field 206. Furthermore, detecting module 106 may detect subsequent reflection 224 by determining a time of a secondary peak in the signal produced by the photodetector (e.g., secondary peak 230 in photodetector signal 226) during a secondary period of the scan of scanning field 206.

To illustrate, at a time when photodetector 160 is not receiving a reflection from eye 212, photodetector 160 may output a null or low-level signal. Detecting module 106 may receive this low-level signal and may determine that photodetector 160 has not received a reflection from eye 212 at the time of the output of the low-level signal. However, when the photodetector detects a reflection from eye 212 (e.g., initial reflection 222 and/or subsequent reflection 224), photodetector 160 may output a peak or higher-level signal (e.g., a signal that varies from the low-level signal by a threshold amount). Detecting module 106 may receive this peak signal and may determine that the photodetector 160 received a reflection from eye 212 at a time of the peak.

For example, directing module 104 may direct scanning device 140 to execute a scan of line of light 204 across scanning field 206 in scanning direction 208. During a primary period of the scan, line of light 204 may scan across eye 212 in primary direction 214, and detecting module 106 may receive a signal from photodetector 160. At a primary time during the primary period, photodetector 160 may receive initial reflection 222, causing primary peak 228 in photodetector signal 226. Detecting module 106 may therefore detect initial reflection 222 by determining a time of primary peak 228. Likewise, during a secondary period of the scan, reflector 216 may reflect line of light 204 such that reflection 218 of line of light 204 scans across eye 212 in secondary direction 220. At a secondary time during the secondary period, photodetector 160 may receive subsequent reflection 224, causing secondary peak 230 in photodetector signal 226. Detecting module 106 may therefore detect subsequent reflection 224 by determining a time of secondary peak 230.

Returning to FIG. 3, at step 330, one or more of the systems described herein may identify a location on an eye based on at least one of an initial reflection and a subsequent reflection. For example, identifying module 108 may, as part of control device 202, identify location 232 based on at least one of initial reflection 222 and subsequent reflection 224.

Identifying module 108 may identify location 232 based on at least one of initial reflection 222 and subsequent reflection 224 in a variety of contexts. For example, identifying module 108 may identify location 232 by associating a primary location on eye 212 that line of light 204 illuminated at a time that detecting module 106 detected initial reflection 222 with a secondary location on eye 212 that reflection 218 illuminated at a time that detecting module 106 detected subsequent reflection 224.

For example, as illustrated by FIG. 5, at a particular time during the primary period of the scan, line of light 204 may illuminate a portion of eye 212 that corresponds to the shape of line of light 204. At the particular time, photodetector 160 (e.g., a particular photosensitive element included in photodetector 160) may receive initial reflection 222, causing detecting module 106 to detect initial reflection 222 at the particular time. This may indicate that initial reflection 222 was reflected by a portion of eye 212 illuminated by line of light 204 at the particular time (e.g., by a portion of eye 212 along line of light 204).

As illustrated by FIG. 7, at an additional time during the secondary period of the scan, reflection 218 may illuminate an additional portion of eye 212 that corresponds to the shape of reflection 218. At the additional time during the secondary period of the scan, photodetector 160 (e.g., a particular photosensitive element included in photodetector 160) may receive subsequent reflection 224, causing detecting module 106 to detect subsequent reflection 224 at the additional time. This may indicate that subsequent reflection 224 was reflected by a portion of eye 212 illuminated by reflection 218 at the additional time (e.g., by a portion of eye 212 illuminated by reflection 218). The additional portion of eye 212 illuminated by reflection 218 at the additional time may intersect and/or overlap with the portion of eye 212 that corresponds to the path of line of light 204 at the particular time during the primary period of the scan. Identifying module 108 may identify the portion of eye 212 that corresponds to the intersection of line of light 204 and the path of reflection 218 as location 232.

In additional embodiments, identifying module 108 may further identify location 232 and/or track a motion of eye 212 based on initial reflection 222, subsequent reflection 224, a point of rotation associated with scanning device 140 (e.g., point of rotation 234), and/or a position of photodetector 160 (e.g., a position of a photosensitive element included in photodetector 160). For example, in at least one embodiment, identifying module 108 may identify location 232 by determining a primary normal angle associated with a primary portion of eye 212 that produced initial reflection 222. Identifying module 108 may determine the primary normal angle based on a position of a point of rotation associated with scanning device 140 (e.g., point of rotation 234), an angle of a projection of line of light 204 from point of rotation 234 at a time of detection of initial reflection 222, and a position of photodetector 160 relative to point of rotation 234.

Figure 10:
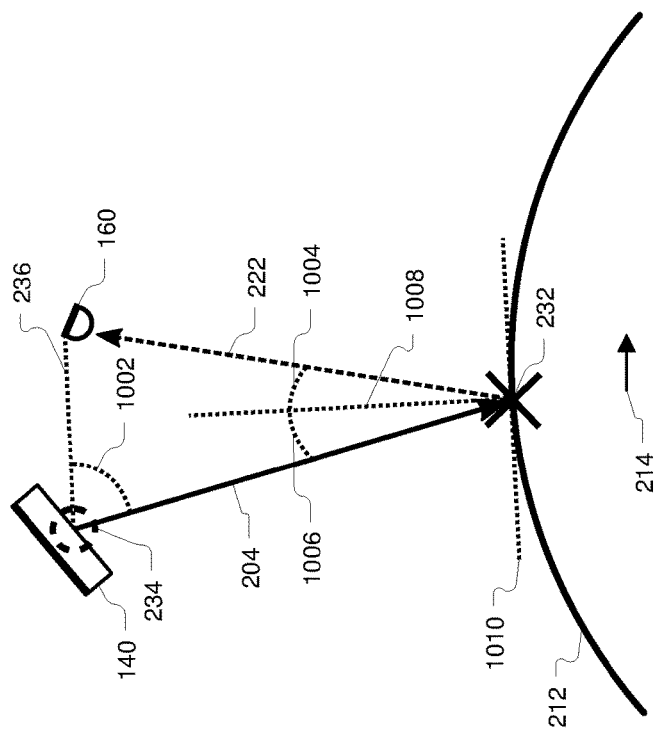
FIGS. 10-11 illustrate identifying a location on an eye based on at least one of the initial reflection and the subsequent reflection in accordance with some embodiments described herein.

By way of illustration, FIG. 10 shows a view 1000 of a possible configuration of scanning device 140, photodetector 160, and eye 212 at a time that photodetector 160 detects initial reflection 222. As shown, photodetector 160 is positioned at photodetector position 236 relative to point of rotation 234 (e.g., a distance and angle from point of rotation 234 to photodetector 160), and scanning device 140 is causing line of light 204 (e.g., a projection of line of light 204) to scan across eye 212 in primary direction 214. A portion of eye 212 has reflected light from line of light 204 (e.g., a ray of light included in line of light 204) toward photodetector 160 as initial reflection 222. At the time that photodetector 160 detects initial reflection 222, a projection of line of light 204 from scanning device 140 may be at a projection angle 1002 relative to photodetector position 236 (e.g., a distance and angle from point of rotation 234 to photodetector 160). In accordance with principles of reflection, the surface of eye 212 may reflect line of light 204 (e.g., a ray of light included in line of light 204) at an angle of reflection 1004 equal to an angle of incidence 1006, where both the angle of reflection 1004 and angle of incidence 1006 are relative to a normal line 1008. Normal line 1008 may be perpendicular to a tangent line 1010 of eye 212 at location 232.

As projection angle 1002, angle of reflection 1004, angle of incidence 1006, normal line 1008, and photodetector position 236 relative to point of rotation 234 may all be known values at the time that photodetector 160 may detect initial reflection 222, identifying module 108 may solve for and/or identify location 232 as a unique location on eye 212 that may be correlated with tangent line 1010 at the time of detection of initial reflection 222.

In additional embodiments, identifying module 108 may identify a secondary location on eye 212 based on subsequent reflection 224 and an apparent position of an apparent point of rotation associated with reflection 218 (e.g., apparent point of rotation 238). Returning to FIG. 2B, during the secondary period of the scan of line of light 204 across scanning field 206, line of light 204 may intersect reflector 216, causing reflection 218 to scan across eye 212 in secondary direction 220. However, reflection 218 may appear to have apparent point of rotation 238 as a point of rotation rather than point of rotation 234. Therefore, although reflection 218 may scan across eye 212 in a substantially mirrored path from a path of line of light 204 across eye 212, and photodetector 160 may detect a subsequent reflection 224, an angle between a projection of reflection 218 from apparent point of rotation 238 may be different from an angle of a projection of line of light 204 from point of rotation 234. This may result in a different location on eye 212 causing subsequent reflection 224 than location 232. Hence, identifying module 108 may identify a secondary location on eye 212 based on subsequent reflection 224 and apparent point of rotation 238 (e.g., a position of apparent point of rotation 238 relative to photodetector 160).

Identifying module 108 may identify an apparent position of apparent point of rotation 238 in any suitable way. For example, identifying module 108 may identify the apparent position of apparent point of rotation 238 based on a position (e.g., a location and an angle) of reflector 216 relative to a position of one or more of line source 150, scanning device 140, and/or photodetector 160.

Figure 11:
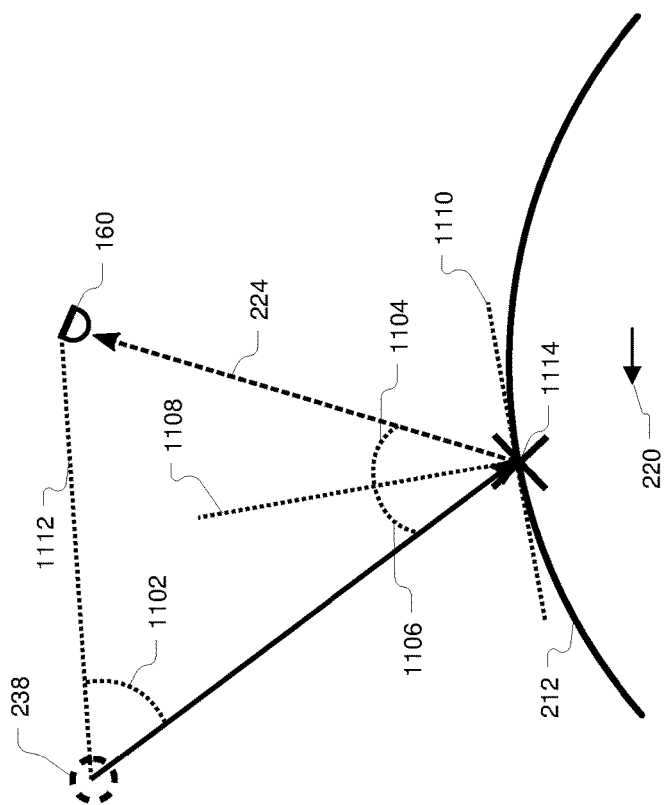

As an illustration, FIG. 11 shows a view 1100 of a possible configuration of apparent point of rotation 238, photodetector 160, and eye 212 at a time that photodetector 160 detects subsequent reflection 224. As shown, photodetector 160 is positioned at photodetector position 1112 relative to apparent point of rotation 238 (e.g., a distance and angle from apparent point of rotation 238 to photodetector 160). Although photodetector position 1112 may represent a different angle and distance than photodetector position 236, photodetector 160 may be in the same location relative to other components of system 200 (e.g., line source 150, scanning device 140, reflector 216, etc.) in both FIG. 10 and FIG. 11.

As further shown in FIG. 11, scanning device 140 may be causing reflection 218 (e.g., a projection of reflection 218 from apparent point of rotation 238) to scan across eye 212 in secondary direction 220. A portion of eye 212 has reflected light from reflection 218 (e.g., a ray of light included in reflection 218) toward photodetector 160 as subsequent reflection 224. At the time that photodetector 160 detects subsequent reflection 224, a projection of reflection 218 from apparent point of rotation 238 may be at a projection angle 1102 relative to apparent point of rotation 238 (e.g., a distance and angle from apparent point of rotation 238 to photodetector 160). In accordance with principles of reflection, the surface of eye 212 may reflect reflection 218 (e.g., a ray of light included in reflection 218) at an angle of reflection 1104 equal to an angle of incidence 1106, where both the angle of reflection 1104 and angle of incidence 1106 are relative to a normal line 1108. Normal line 1108 may be perpendicular to a tangent line 1110 of eye 212 at location 1114.

As projection angle 1102, angle of reflection 1104, angle of incidence 1106, normal line 1108, and photodetector position 1112 relative to apparent point of rotation 238 may all be known values at the time that photodetector 160 may detect initial reflection 222, identifying module 108 may solve for and/or identify secondary location 1114 as a unique location on eye 212 that may be correlated with tangent line 1110 at the time of detection of subsequent reflection 224.

In some embodiments, identifying module 108 may further track a motion of eye 212 based on at least one of the identified location on eye 212 (e.g., location 232) and the identified secondary location on eye 212 (e.g., secondary corneal location 1114). For example, during an initial scan of scanning field 206, identifying module 108 may identify location 232 and secondary location 1114. Identifying module 108 may further identify and/or determine a relationship (e.g., a spatial relationship) between location 232 and secondary location 1114.

During a subsequent scan of scanning field 206, identifying module 108 may identify an additional two locations on eye 212, and may determine that the additional two locations are not at the same locations as location 232 and secondary corneal location 1114. However, identifying module 108 may also determine that a relationship between the additional two locations on eye 212 is similar to the relationship between location 232 and secondary corneal location 1114. Hence, identifying module 108 may conclude that the cornea of eye 212 has moved (e.g., rotated about a rotational axis associated with an eye that includes eye 212), and may track the movement by determining a difference between location 232 and secondary corneal location 1114 and the additional two corneal locations.

In some examples, one or more of the systems described herein (e.g., directing module 104) may also direct scanning device 140 to execute a return scan of line of light 204 across scanning field 206 in a return direction. The return direction may be an opposing direction (e.g., an opposite direction of rotation, an opposite linear direction, etc.) from scanning direction 208. At the conclusion of the return scan, line of light 204 may be located at a starting location for an additional scan.

During a primary period of the return scan, reflector 216 may reflect line of light 204 such that, during a primary return period of the return scan, an additional reflection of line of light 204 may scan across eye 212 in primary direction 214. During a secondary return period of the return scan, line of light 204 may scan across eye 212 in secondary direction 220. Furthermore, one or more of the systems described herein (e.g., detecting module 106) may detect, via photodetector 160, an additional initial reflection produced by the additional reflection of the line of light 204 during the primary return period of the return scan and an additional subsequent reflection produced by line of light 204 during the secondary period of the return scan.

In at least this way, the apparatuses, systems, and methods described herein may execute repeated, oscillating scans of eye 212 in both primary direction 214 and secondary direction 220. One or more reflections from eye 212 may be detected during each scan, and one or more locations on eye 212 may be identified during each scan in accordance with the apparatuses, systems, and methods described herein. In some examples, these oscillating scans, detecting of reflections from eye 212, and/or identifying of locations on eye 212 may occur at any suitable scan rate, such as, without limitation, 1 Hz, 10 Hz, 100 Hz, 1 kHz, 10 kHz, 100 kHz, 1 MHz, and so forth.

As noted above, in some embodiments, a line source, a scanning device, a reflector, and a photodetector may be included in a head-mounted display. In some embodiments, the head-mounted display may include a waveguide display. In some such examples, scanning device 140 may illuminate eye 212 via an optical pathway of the waveguide display and/or photodetector 160 may receive light reflected by eye 212 via the optical pathway of the waveguide display.

Figure 12:
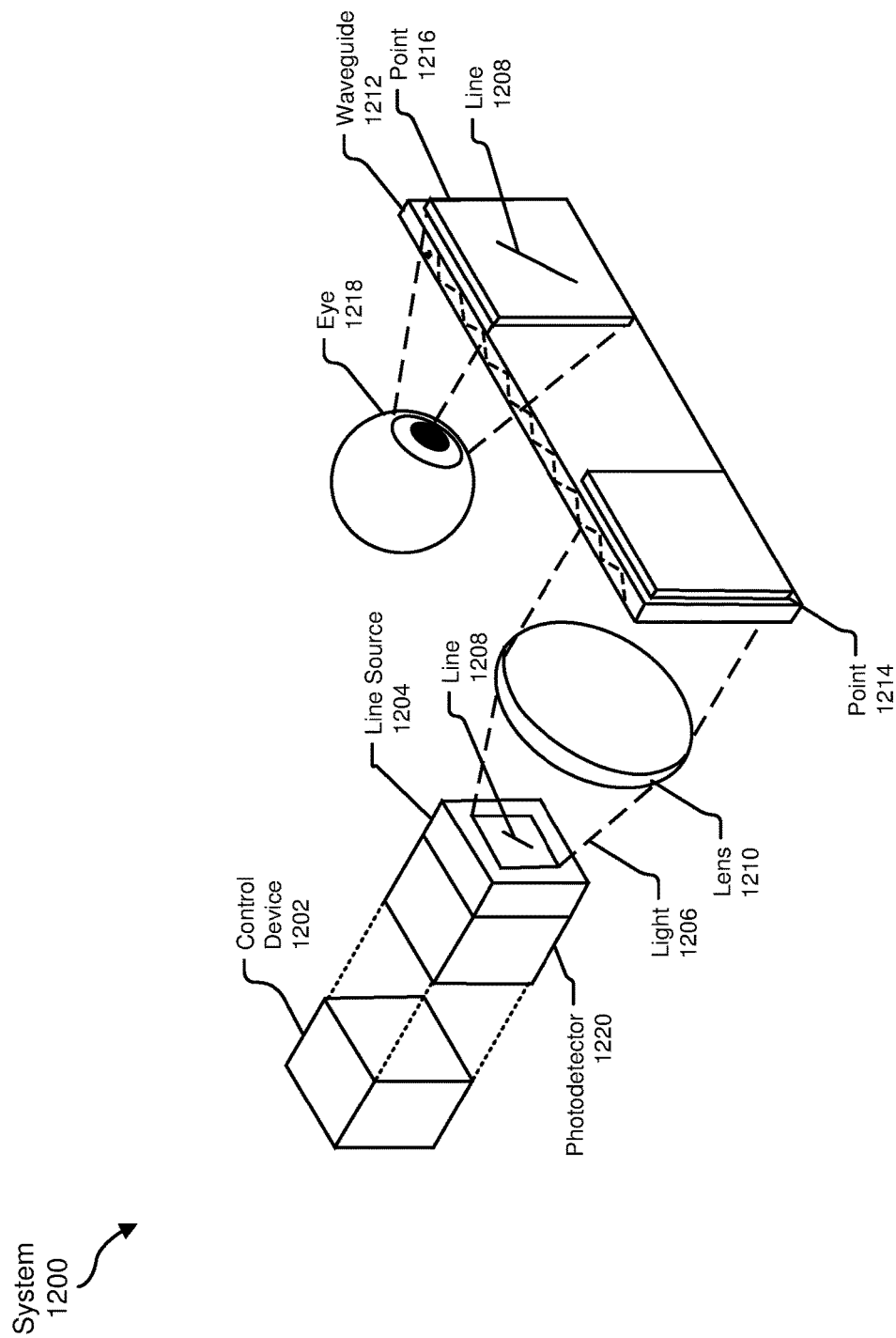
FIG. 12 is an illustration of a waveguide display in accordance with embodiments of this disclosure.

To illustrate, FIG. 12 is a block diagram of an example system 1200 that includes a waveguide display. As shown, example system 1200 includes a control device 1202 that may perform any of the operations described herein associated with control device 202. Example system 1200 may also include a scanning device 1204 that may perform any of the functions described herein with reference to line source 150, scanning device 140, and reflector 216. For example, scanning device 1204 may include (1) an infrared light source such as an infrared VCSEL, (2) a MEMS micromirror device that may be configured to form infrared light from the infrared light source into a line of light and scan the line of light across a surface (e.g., a cornea) in a primary direction, and (3) a reflector that may reflect the line of light such that a reflection of the line of light may scan across the cornea in a secondary direction.

Scanning device 1204 may generate and/or produce light 1206 that may include a projection of a line of light 1208 (also "line 1208" herein). Light 1206 and/or the projection of line 1208 may pass through a lens 1210, which may represent one or more optical elements that may direct light 1206 into waveguide 1212. Waveguide 1212 may include any suitable waveguide that may guide waves in a portion of the electromagnetic spectrum from a first point (e.g., point 1214) to a second point (e.g., point 1216) via any suitable mechanism, such as internal reflection, Bragg reflection, and so forth. Hence, waveguide 1212 may guide light from point 1214 to point 1216 and/or from point 1216 to point 1214. Light may exit waveguide 1212 at point 1216, and waveguide 1212 and/or any other suitable optical elements (e.g., a combiner lens) may direct the light toward an eye of a user, such as eye 1218. Likewise, light may exit waveguide 1212 at point 1214, and waveguide 1212 may direct the exiting light toward a photodetector 1220 (e.g., via lens 1210).

Hence, directing module 104 may direct scanning device 1204 to execute a scan of a line of light across a scanning field in a scanning direction by directing scanning device 1204 to generate and/or produce a projection of a line and direct the projection of the line toward point 1214 of waveguide 1212. Light that includes the projection of the line (e.g., light 1206 that may include line 1208) may enter waveguide 1212, and waveguide 1212 may guide the light toward point 1216. Upon exiting waveguide 1212 at point 1216, line 1208 may scan across eye 1218 in a primary direction during a primary period of the scan. Furthermore, during the secondary period of the scan, a reflector included in scanning device 1204 may reflect line 1208 such that a reflection of line 1208 may follow the same optical path from scanning device 1204 to eye 1218 and may scan across eye 1218 in a secondary direction.

Furthermore, eye 1218 (e.g., a tear-air interface of a cornea of eye 1218) may reflect light from line 1208 and/or the reflection of line 1208 back into waveguide 1212 at point 1216. Waveguide 1212 may guide the reflected light toward point 1214, where the reflected light may exit waveguide 1212 and/or pass into lens 1210. Lens 1210 may direct the reflected light toward photodetector 1220. Detecting module 106 may therefore detect, via photodetector 1220, a portion of the projection of line 1208 and/or the reflection of line 1208 reflected by eye 1218 (e.g., an initial reflection and a subsequent reflection). Identifying module 108 may then identify a location on eye 1218 in any of the ways described herein. Additional examples of waveguides and/or waveguide displays may be described below in reference to FIGS. 14-15.

Embodiments of the present disclosure may include or be implemented in conjunction with various types of artificial reality systems. Artificial reality is a form of reality that has been adjusted in some manner before presentation to a user, which may include, e.g., a virtual reality, an augmented reality, a mixed reality, a hybrid reality, or some combination and/or derivative thereof. Artificial-reality content may include completely generated content or generated content combined with captured (e.g., real-world) content. The artificial-reality content may include video, audio, haptic feedback, or some combination thereof, any of which may be presented in a single channel or in multiple channels (such as stereo video that produces a three-dimensional effect to the viewer). Additionally, in some embodiments, artificial reality may also be associated with applications, products, accessories, services, or some combination thereof, that are used to, e.g., create content in an artificial reality and/or are otherwise used in (e.g., to perform activities in) an artificial reality.

Artificial-reality systems may be implemented in a variety of different form factors and configurations. Some artificial reality systems may be designed to work without near-eye displays (NEDs), an example of which is augmented-reality system 1300 in FIG. 13. Other artificial reality systems may include a NED that also provides visibility into the real world (e.g., augmented-reality system 1400 in FIG. 14) or that visually immerses a user in an artificial reality (e.g., virtual-reality system 1500 in FIG. 15). While some artificial-reality devices may be self-contained systems, other artificial-reality devices may communicate and/or coordinate with external devices to provide an artificial-reality experience to a user. Examples of such external devices include handheld controllers, mobile devices, desktop computers, devices worn by a user, devices worn by one or more other users, and/or any other suitable external system.

Figure 13:
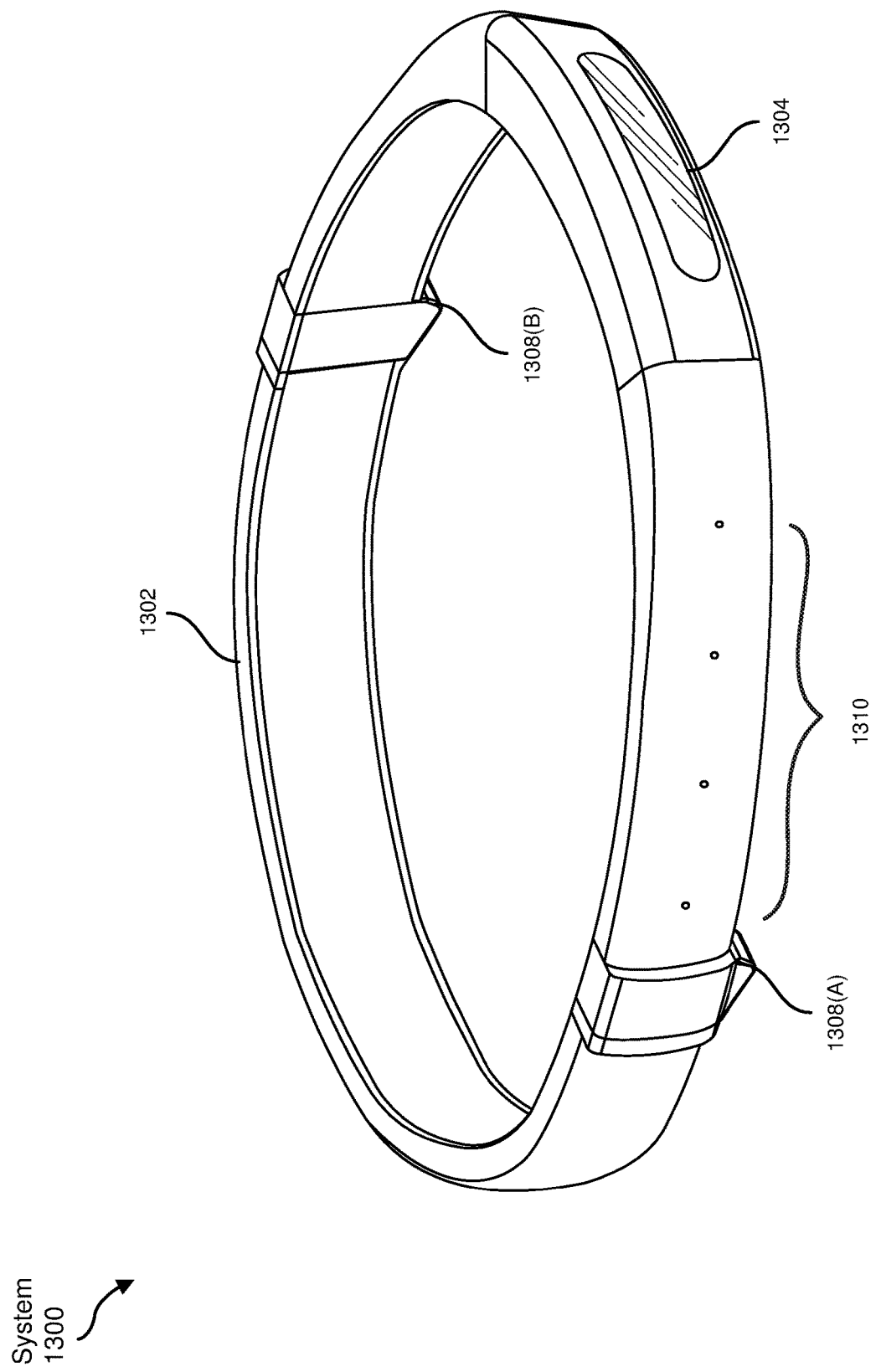
FIG. 13 is an illustration of an example artificial-reality headband that may be used in connection with embodiments of this disclosure.

Turning to FIG. 13, augmented-reality system 1300 generally represents a wearable device dimensioned to fit about a body part (e.g., a head) of a user. As shown in FIG. 13, system 1300 may include a frame 1302 and a camera assembly 1304 that is coupled to frame 1302 and configured to gather information about a local environment by observing the local environment. Augmented-reality system 1300 may also include one or more audio devices, such as output audio transducers 1308(A) and 1308(B) and input audio transducers 1310. Output audio transducers 1308(A) and 1308(B) may provide audio feedback and/or content to a user, and input audio transducers 1310 may capture audio in a user's environment.

As shown, augmented-reality system 1300 may not necessarily include a NED positioned in front of a user's eyes. Augmented-reality systems without NEDs may take a variety of forms, such as head bands, hats, hair bands, belts, watches, wrist bands, ankle bands, rings, neckbands, necklaces, chest bands, eyewear frames, and/or any other suitable type or form of apparatus. While augmented-reality system 1300 may not include a NED, augmented-reality system 1300 may include other types of screens or visual feedback devices (e.g., a display screen integrated into a side of frame 1302).

Figure 14:
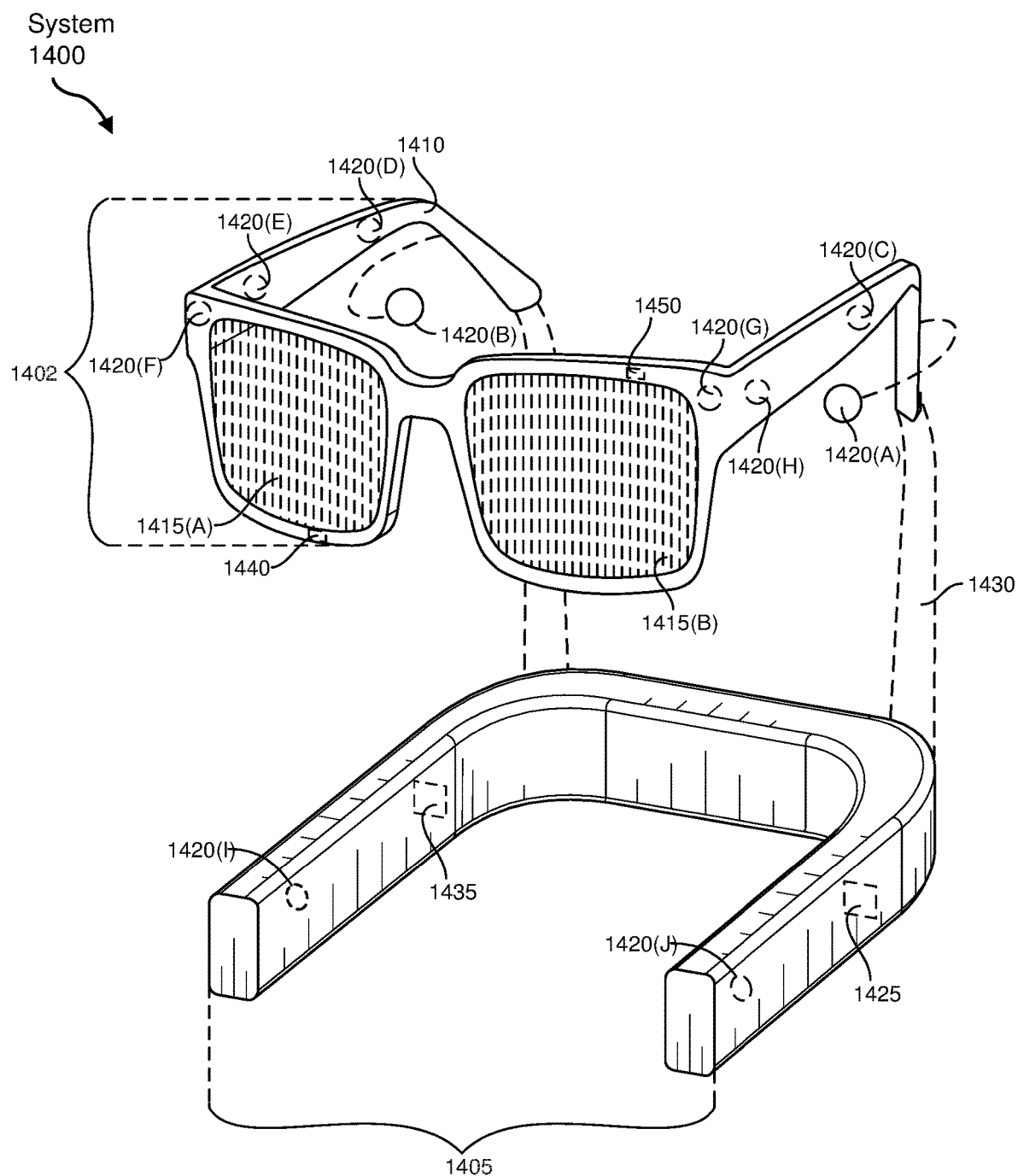
FIG. 14 is an illustration of example augmented-reality glasses that may be used in connection with embodiments of this disclosure.

The embodiments discussed in this disclosure may also be implemented in augmented-reality systems that include one or more NEDs. For example, as shown in FIG. 14, augmented-reality system 1400 may include an eyewear device 1402 with a frame 1410 configured to hold a left display device 1415(A) and a right display device 1415(B) in front of a user's eyes. Display devices 1415(A) and 1415(B) may act together or independently to present an image or series of images to a user. While augmented-reality system 1400 includes two displays, embodiments of this disclosure may be implemented in augmented-reality systems with a single NED or more than two NEDs.

In some embodiments, augmented-reality system 1400 may include one or more sensors, such as sensor 1440. Sensor 1440 may generate measurement signals in response to motion of augmented-reality system 1400 and may be located on substantially any portion of frame 1410. Sensor 1440 may represent a position sensor, an inertial measurement unit (IMU), a depth camera assembly, or any combination thereof. In some embodiments, augmented-reality system 1400 may or may not include sensor 1440 or may include more than one sensor. In embodiments in which sensor 1440 includes an IMU, the IMU may generate calibration data based on measurement signals from sensor 1440. Examples of sensor 1440 may include, without limitation, accelerometers, gyroscopes, magnetometers, other suitable types of sensors that detect motion, sensors used for error correction of the IMU, or some combination thereof.

Augmented-reality system 1400 may also include a microphone array with a plurality of acoustic transducers 1420(A)-1420(J), referred to collectively as acoustic transducers 1420. Acoustic transducers 1420 may be transducers that detect air pressure variations induced by sound waves. Each acoustic transducer 1420 may be configured to detect sound and convert the detected sound into an electronic format (e.g., an analog or digital format). The microphone array in FIG. 2 may include, for example, ten acoustic transducers: 1420(A) and 1420(B), which may be designed to be placed inside a corresponding ear of the user, acoustic transducers 1420(C), 1420(D), 1420(E), 1420(F), 1420(G), and 1420(H), which may be positioned at various locations on frame 1410, and/or acoustic transducers 1420(I) and 1420(J), which may be positioned on a corresponding neckband 1405.

In some embodiments, one or more of acoustic transducers 1420(A)-(F) may be used as output transducers (e.g., speakers). For example, acoustic transducers 1420(A) and/or 1420(B) may be earbuds or any other suitable type of headphone or speaker.

The configuration of acoustic transducers 1420 of the microphone array may vary. While augmented-reality system 1400 is shown in FIG. 14 as having ten acoustic transducers 1420, the number of acoustic transducers 1420 may be greater or less than ten. In some embodiments, using higher numbers of acoustic transducers 1420 may increase the amount of audio information collected and/or the sensitivity and accuracy of the audio information. In contrast, using a lower number of acoustic transducers 1420 may decrease the computing power required by the controller 1450 to process the collected audio information. In addition, the position of each acoustic transducer 1420 of the microphone array may vary. For example, the position of an acoustic transducer 1420 may include a defined position on the user, a defined coordinate on frame 1410, an orientation associated with each acoustic transducer, or some combination thereof.

Acoustic transducers 1420(A) and 1420(B) may be positioned on different parts of the user's ear, such as behind the pinna or within the auricle or fossa. Or, there may be additional acoustic transducers on or surrounding the ear in addition to acoustic transducers 1420 inside the ear canal. Having an acoustic transducer positioned next to an ear canal of a user may enable the microphone array to collect information on how sounds arrive at the ear canal. By positioning at least two of acoustic transducers 1420 on either side of a user's head (e.g., as binaural microphones), augmented-reality device 1400 may simulate binaural hearing and capture a 3D stereo sound field around about a user's head. In some embodiments, acoustic transducers 1420(A) and 1420(B) may be connected to augmented-reality system 1400 via a wired connection 1430, and in other embodiments, acoustic transducers 1420(A) and 1420(B) may be connected to augmented-reality system 1400 via a wireless connection (e.g., a Bluetooth connection). In still other embodiments, acoustic transducers 1420(A) and 1420(B) may not be used at all in conjunction with augmented-reality system 1400.

Acoustic transducers 1420 on frame 1410 may be positioned along the length of the temples, across the bridge, above or below display devices 1415(A) and 1415(B), or some combination thereof. Acoustic transducers 1420 may be oriented such that the microphone array is able to detect sounds in a wide range of directions surrounding the user wearing the augmented-reality system 1400. In some embodiments, an optimization process may be performed during manufacturing of augmented-reality system 1400 to determine relative positioning of each acoustic transducer 1420 in the microphone array.

In some examples, augmented-reality system 1400 may include or be connected to an external device (e.g., a paired device), such as neckband 1405. Neckband 1405 generally represents any type orform of paired device. Thus, the following discussion of neckband 1405 may also apply to various other paired devices, such as charging cases, smart watches, smart phones, wrist bands, other wearable devices, hand-held controllers, tablet computers, laptop computers and other external compute devices, etc.

As shown, neckband 1405 may be coupled to eyewear device 1402 via one or more connectors. The connectors may be wired or wireless and may include electrical and/or non-electrical (e.g., structural) components. In some cases, eyewear device 1402 and neckband 1405 may operate independently without any wired or wireless connection between them. While FIG. 14 illustrates the components of eyewear device 1402 and neckband 1405 in example locations on eyewear device 1402 and neckband 1405, the components may be located elsewhere and/or distributed differently on eyewear device 1402 and/or neckband 1405. In some embodiments, the components of eyewear device 1402 and neckband 1405 may be located on one or more additional peripheral devices paired with eyewear device 1402, neckband 1405, or some combination thereof. Furthermore, Pairing external devices, such as neckband 1405, with augmented-reality eyewear devices may enable the eyewear devices to achieve the form factor of a pair of glasses while still providing sufficient battery and computation power for expanded capabilities. Some or all of the battery power, computational resources, and/or additional features of augmented-reality system 1400 may be provided by a paired device or shared between a paired device and an eyewear device, thus reducing the weight, heat profile, and form factor of the eyewear device overall while still retaining desired functionality. For example, neckband 1405 may allow components that would otherwise be included on an eyewear device to be included in neckband 1405 since users may tolerate a heavier weight load on their shoulders than they would tolerate on their heads. Neckband 1405 may also have a larger surface area over which to diffuse and disperse heat to the ambient environment. Thus, neckband 1405 may allow for greater battery and computation capacity than might otherwise have been possible on a stand-alone eyewear device. Since weight carried in neckband 1405 may be less invasive to a user than weight carried in eyewear device 1402, a user may tolerate wearing a lighter eyewear device and carrying or wearing the paired device for greater lengths of time than a user would tolerate wearing a heavy stand-alone eyewear device, thereby enabling users to more fully incorporate artificial reality environments into their day-to-day activities.

Neckband 1405 may be communicatively coupled with eyewear device 1402 and/or to other devices. These other devices may provide certain functions (e.g., tracking, localizing, depth mapping, processing, storage, etc.) to augmented-reality system 1400. In the embodiment of FIG. 14, neckband 1405 may include two acoustic transducers (e.g., 1420(I) and 1420(J)) that are part of the microphone array (or potentially form their own microphone subarray). Neckband 1405 may also include a controller 1425 and a power source 1435.

Acoustic transducers 1420( ) and 1420(J) of neckband 1405 may be configured to detect sound and convert the detected sound into an electronic format (analog or digital). In the embodiment of FIG. 14, acoustic transducers 1420(I) and 1420(J) may be positioned on neckband 1405, thereby increasing the distance between the neckband acoustic transducers 1420( ) and 1420(J) and other acoustic transducers 1420 positioned on eyewear device 1402. In some cases, increasing the distance between acoustic transducers 1420 of the microphone array may improve the accuracy of beamforming performed via the microphone array. For example, if a sound is detected by acoustic transducers 1420(C) and 1420(D) and the distance between acoustic transducers 1420(C) and 1420(D) is greater than, e.g., the distance between acoustic transducers 1420(D) and 1420(E), the determined source location of the detected sound may be more accurate than if the sound had been detected by acoustic transducers 1420(D) and 1420(E).

Controller 1425 of neckband 1405 may process information generated by the sensors on neckband 1405 and/or augmented-reality system 1400. For example, controller 1425 may process information from the microphone array that describes sounds detected by the microphone array. For each detected sound, controller 1425 may perform a direction-of-arrival (DOA) estimation to estimate a direction from which the detected sound arrived at the microphone array. As the microphone array detects sounds, controller 1425 may populate an audio data set with the information. In embodiments in which augmented-reality system 1400 includes an inertial measurement unit, controller 1425 may compute all inertial and spatial calculations from the IMU located on eyewear device 1402. A connector may convey information between augmented-reality system 1400 and neckband 1405 and between augmented-reality system 1400 and controller 1425. The information may be in the form of optical data, electrical data, wireless data, or any other transmittable data form. Moving the processing of information generated by augmented-reality system 1400 to neckband 1405 may reduce weight and heat in eyewear device 1402, making it more comfortable to the user.

Power source 1435 in neckband 1405 may provide power to eyewear device 1402 and/or to neckband 1405. Power source 1435 may include, without limitation, lithium ion batteries, lithium-polymer batteries, primary lithium batteries, alkaline batteries, or any other form of power storage. In some cases, power source 1435 may be a wired power source. Including power source 1435 on neckband 1405 instead of on eyewear device 1402 may help better distribute the weight and heat generated by power source 1435.

As noted, some artificial reality systems may, instead of blending an artificial reality with actual reality, substantially replace one or more of a user's sensory perceptions of the real world with a virtual experience. One example of this type of system is a head-worn display system, such as virtual-reality system 1500 in FIG. 15, that mostly or completely covers a user's field of view. Virtual-reality system 1500 may include a front rigid body 1502 and a band 1504 shaped to fit around a user's head. Virtual-reality system 1500 may also include output audio transducers 1506(A) and 1506(B). Furthermore, while not shown in FIG. 15, front rigid body 1502 may include one or more electronic elements, including one or more electronic displays, one or more inertial measurement units (IMUs), one or more tracking emitters or detectors, and/or any other suitable device or system for creating an artificial reality experience.

Artificial reality systems may include a variety of types of visual feedback mechanisms. For example, display devices in augmented-reality system 1500 and/or virtual-reality system 1500 may include one or more liquid crystal displays (LCDs), light emitting diode (LED) displays, organic LED (OLED) displays, and/or any other suitable type of display screen. Artificial reality systems may include a single display screen for both eyes or may provide a display screen for each eye, which may allow for additional flexibility for varifocal adjustments or for correcting a user's refractive error. Some artificial reality systems may also include optical subsystems having one or more lenses (e.g., conventional concave or convex lenses, Fresnel lenses, adjustable liquid lenses, etc.) through which a user may view a display screen.

In addition to or instead of using display screens, some artificial reality systems may include one or more projection systems. For example, display devices in augmented-reality system 1400 and/or virtual-reality system 1500 may include micro-LED projectors that project light (using, e.g., a waveguide) into display devices, such as clear combiner lenses that allow ambient light to pass through. The display devices may refract the projected light toward a user's pupil and may enable a user to simultaneously view both artificial reality content and the real world. Artificial reality systems may also be configured with any other suitable type or form of image projection system.

Artificial reality systems may also include various types of computer vision components and subsystems. For example, augmented-reality system 1300, augmented-reality system 1400, and/or virtual-reality system 1500 may include one or more optical sensors, such as two-dimensional (2D) or three-dimensional (3D) cameras, time-of-flight depth sensors, single-beam or sweeping laser rangefinders, 3D LiDAR sensors, and/or any other suitable type or form of optical sensor. An artificial reality system may process data from one or more of these sensors to identify a location of a user, to map the real world, to provide a user with context about real-world surroundings, and/or to perform a variety of other functions.

Artificial reality systems may also include one or more input and/or output audio transducers. In the examples shown in FIGS. 13 and 15, output audio transducers 1308(A), 1308(B), 1506(A), and 1506(B) may include voice coil speakers, ribbon speakers, electrostatic speakers, piezoelectric speakers, bone conduction transducers, cartilage conduction transducers, and/or any other suitable type or form of audio transducer. Similarly, input audio transducers 1310 may include condenser microphones, dynamic microphones, ribbon microphones, and/or any other type or form of input transducer. In some embodiments, a single transducer may be used for both audio input and audio output.

Figure 15:
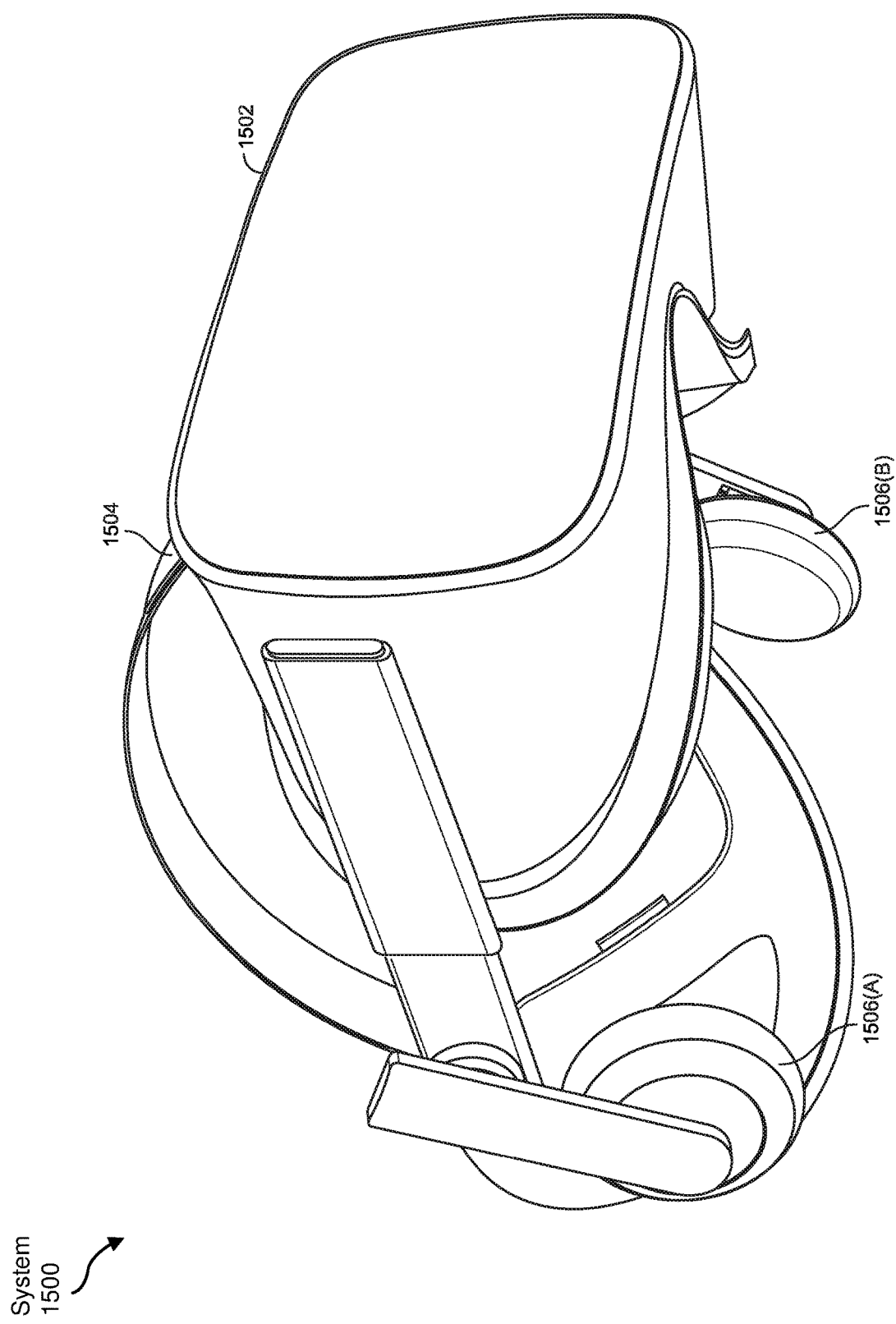
FIG. 15 is an illustration of an example virtual-reality headset that may be used in connection with embodiments of this disclosure.

While not shown in FIGS. 13-15, artificial reality systems may include tactile (i.e., haptic) feedback systems, which may be incorporated into headwear, gloves, body suits, handheld controllers, environmental devices (e.g., chairs, floormats, etc.), and/or any other type of device or system. Haptic feedback systems may provide various types of cutaneous feedback, including vibration, force, traction, texture, and/or temperature. Haptic feedback systems may also provide various types of kinesthetic feedback, such as motion and compliance. Haptic feedback may be implemented using motors, piezoelectric actuators, fluidic systems, and/or a variety of other types of feedback mechanisms. Haptic feedback systems may be implemented independent of other artificial reality devices, within other artificial reality devices, and/or in conjunction with other artificial reality devices.

By providing haptic sensations, audible content, and/or visual content, artificial reality systems may create an entire virtual experience or enhance a user's real-world experience in a variety of contexts and environments. For instance, artificial reality systems may assist or extend a user's perception, memory, or cognition within a particular environment. Some systems may enhance a user's interactions with other people in the real world or may enable more immersive interactions with other people in a virtual world. Artificial reality systems may also be used for educational purposes (e.g., for teaching or training in schools, hospitals, government organizations, military organizations, business enterprises, etc.), entertainment purposes (e.g., for playing video games, listening to music, watching video content, etc.), and/or for accessibility purposes (e.g., as hearing aids, visuals aids, etc.). The embodiments disclosed herein may enable or enhance a user's artificial reality experience in one or more of these contexts and environments and/or in other contexts and environments.

As discussed throughout the instant disclosure, the disclosed apparatuses, systems, and methods may provide one or more advantages over traditional options for scanning a cornea (e.g., with a line of light). For example, by enabling multiple orthogonal sweeps of a cornea during a single scan of a line source across a scanning field in a single direction, the apparatuses, systems, and methods described herein may efficiently identify, in two dimensions, locations on a cornea while realizing power savings through only scanning in a single direction. These multiple scans may enable identification and/or tracking of specific points on the cornea, tracking of a motion of the cornea, identification of a gaze direction of the eye, and so forth, with improved efficiency in comparison to conventional corneal scanning solutions that may require multiple scans of the cornea.

Furthermore, in some examples, the apparatuses, systems, and methods described herein may generate sparse signals associated with detected reflections, such that data representative of detected reflections may be sparse and easily processed by comparatively low power computing devices such as mobile or embedded computing devices. Hence, the apparatuses, systems, and methods described herein may reduce power consumption associated with conventional corneal scanning eye tracking systems and may reduce computing requirements associated with conventional eye tracking systems.

Furthermore, the apparatuses, systems, and methods described herein may use one or more photodetectors that may output signals based on differences in light received by the photodetectors rather than an absolute amount of light received by the photodetectors. Hence, even in situations where a level of ambient light may be relatively high (e.g., daylight), the photodetectors may still detect reflections received from an eye as the photodetectors may be able to discriminate between the ambient light and reflections from the eye generated by a line of light as described herein.

EXAMPLE EMBODIMENTS

Example 1: An apparatus comprising (1) a line source configured to produce a line of light, (2) a scanning device configured to scan the line of light across a scanning field in a scanning direction, the scanning field comprising a receiving portion configured to receive an eye of a user, (3) a reflector positioned within the scanning field such that (a) during a primary period of a scan by the scanning device, the line of light scans the receiving portion in a primary direction, (b) during a secondary period of the scan, the reflector reflects the line of light such that a reflection of the line of light scans the receiving portion in a secondary direction, and (4) a photodetector positioned to receive (a) an initial reflection produced by the line of light during the primary period of the scan, and (b) a subsequent reflection produced by the reflection of the line of light during the secondary period of the scan.

Example 2: The apparatus of example 1, further comprising a control device communicatively coupled to the line source, the scanning device, and the photodetector, that (1) directs the scanning device to scan the line of light across the scanning field in the scanning direction, and (2) detects, via the photodetector, the initial reflection and the subsequent reflection, and (3) identifies a location on the eye based on at least one of the initial reflection and the subsequent reflection.

Example 3: The apparatus of example 2, wherein the control device (1) detects the initial reflection by determining a time of a primary peak in a signal produced by the photodetector during the primary period, and (2) detects the subsequent reflection by determining a time of a secondary peak in the signal produced by the photodetector during the secondary period.

Example 4: The apparatus of any of examples 2 or 3, wherein the control device identifies the location on the eye by determining a primary normal angle associated with a primary portion of the eye that produced the initial reflection based on (1) a position of a point of rotation associated with the scanning device, (2) an angle of a projection of the line of light from the point of rotation at a time of detection of the initial reflection, and (3) a position of the photodetector relative to the point of rotation.

Example 5: The apparatus of any of examples 2-4, wherein the control device further identifies a secondary location on the eye by (1) identifying an apparent position of an apparent point of rotation associated with the reflection of the line of light, and (2) determining a primary normal angle associated with a secondary portion of the eye that produced the subsequent reflection based on (a) the apparent position of the apparent point of rotation associated with the reflection of the line of light, and (b) an apparent angle of an apparent projection of the reflection of the line of light from the apparent point of rotation at a time of detection of the subsequent reflection, and (c) an apparent position of the photodetector relative to the apparent point of rotation.

Example 6: The apparatus of example 5, wherein the control device further tracks a motion of the eye based on at least one of the location on the eye and the secondary location on the eye.

Example 7: The apparatus of any of examples 1-6, wherein the line of light is oriented in a primary orientation relative to the primary direction and the reflection of the line of light is oriented in a secondary orientation relative to the primary direction.

Example 8: The apparatus of example 7, wherein the primary orientation is orthogonal in a common plane to the secondary orientation.

Example 9: The apparatus of any of examples 1-8, wherein the photodetector comprises an array of photosensitive elements.

Example 10: The apparatus of example 9, wherein the array of photosensitive elements comprises at least four photosensitive elements.

Example 11: The apparatus of any of examples 1-10, wherein (1) the line source comprises a laser fan source, and (2) the line of light comprises an edge of a laser fan generated by the laser fan source.

Example 12: The apparatus of any of examples 1-11, wherein the line source, the scanning device, the reflector, and the photodetector are included in a head-mounted display worn by a user.

Example 13: The apparatus of example 12, wherein the head-mounted display comprises a waveguide display.

Example 14: A method comprising (1) directing a scanning device to scan a line of light, produced by a line source, across a scanning field in a scanning direction, the scanning field comprising a receiving portion configured to receive an eye of a user, wherein (a) during a primary period of the scan, the line of light scans the receiving portion in a primary direction, and (b) during a secondary period of the scan, a reflector positioned within the scanning field reflects the line of light such that a reflection of the line of light scans the receiving portion in a secondary direction, (2) detecting, via a photodetector (a) an initial reflection produced by the line of light during the primary period, and (b) a subsequent reflection produced by the reflection of the line of light during the secondary period, and (3) identifying a location on the eye based on at least one of the initial reflection and the subsequent reflection.

Example 15: The method of example 14, further comprising (1) directing the scanning device to execute a return scan of the line of light across the scanning field in a return direction, wherein: (a) during a primary return period of the return scan, the reflector reflects the line of light such that an additional reflection of the line of light scans across the receiving portion in the primary direction, and (b) during a secondary return period of the return scan, the line of light scans across the receiving portion in the secondary direction, and (2) detecting, via the photodetector, an additional initial reflection produced by the additional reflection of the line of light during the primary return period of the return scan and an additional subsequent reflection produced by the line of light during the secondary return period of the return scan.

Example 16: The method of any of examples 14 or 15, wherein (1) detecting the initial reflection comprises determining a time of a primary peak in a signal produced by the photodetector during the primary period, and (2) detecting the subsequent reflection comprises determining a time of a secondary peak in the signal produced by the photodetector during the secondary period.

Example 17: The method of any of examples 14-16, wherein identifying the location on the eye comprises determining a primary normal angle associated with a primary portion of the eye that produced the initial reflection based on (1) a position of a point of rotation associated with the scanning device, (2) an angle of a projection of the line of light from the point of rotation at a time of detection of the initial reflection, and (3) a position of the photodetector relative to a position of a point of rotation associated with the scanning device.

Example 18: The method of example 17, further comprising identifying a secondary location on the eye, the identifying of the secondary location on the eye comprising (1) identifying an apparent position of an apparent point of rotation associated with the reflection of the line of light, and (2) determining a primary normal angle associated with a secondary portion of the eye that produced the initial reflection based on (a) the apparent position of the apparent point of rotation associated with the reflection of the line of light, and (b) an angle of a projection of the reflection of the line of light from the apparent point of rotation at a time of detection of the subsequent reflection, and (c) a position of the photodetector relative to the apparent point of rotation.

Example 19: The method of example 18, further comprising tracking a motion of the eye based on at least one of the location on the eye and the secondary location on the eye.

Example 20: A non-transitory computer-readable medium comprising computer-readable instructions that, when executed by at least one processor of a computing system, cause the computing system to (1) direct a scanning device to scan a line of light, produced by a line source, across a scanning field in a scanning direction, the scanning field comprising a receiving portion configured to receive an eye of a user, wherein (a) during a primary period of the scan, the line of light scans the receiving portion in a primary direction, and (b) during a secondary period of the scan, a reflector positioned within the scanning field reflects the line of light such that a reflection of the line of light scans the receiving portion in a secondary direction, (2) detect, via a photodetector (a) an initial reflection produced by the line of light during the primary period, and (b) a subsequent reflection produced by the reflection of the line of light during the secondary period, and (3) identify a location on the eye based on at least one of the initial reflection and the subsequent reflection.

As detailed above, the computing devices and systems described and/or illustrated herein broadly represent any type or form of computing device or system capable of executing computer-readable instructions, such as those contained within the modules described herein. In their most basic configuration, these computing device(s) may each include at least one memory device and at least one physical processor.

Although illustrated as separate elements, the modules described and/or illustrated herein may represent portions of a single module or application. In addition, in certain embodiments one or more of these modules may represent one or more software applications or programs that, when executed by a computing device, may cause the computing device to perform one or more tasks. For example, one or more of the modules described and/or illustrated herein may represent modules stored and configured to run on one or more of the computing devices or systems described and/or illustrated herein. One or more of these modules may also represent all or portions of one or more special-purpose computers configured to perform one or more tasks.

In addition, one or more of the modules described herein may transform data, physical devices, and/or representations of physical devices from one form to another. For example, one or more of the modules recited herein may receive photodetector data to be transformed, transform the photodetector data, output a result of the transformation to identify a location on an eye of a user, use the result of the transformation to track the eye of the user, and store the result of the transformation to further track the eye of the user at a later time. Additionally or alternatively, one or more of the modules recited herein may transform a processor, volatile memory, non-volatile memory, and/or any other portion of a physical computing device from one form to another by executing on the computing device, storing data on the computing device, and/or otherwise interacting with the computing device.

In some embodiments, the term "computer-readable medium" generally refers to any form of device, carrier, or medium capable of storing or carrying computer-readable instructions. Examples of computer-readable media include, without limitation, transmission-type media, such as carrier waves, and non-transitory-type media, such as magnetic-storage media (e.g., hard disk drives, tape drives, and floppy disks), optical-storage media (e.g., Compact Disks (CDs), Digital Video Disks (DVDs), and BLU-RAY disks), electronic-storage media (e.g., solid-state drives and flash media), and other distribution systems.

The process parameters and sequence of the steps described and/or illustrated herein are given by way of example only and can be varied as desired. For example, while the steps illustrated and/or described herein may be shown or discussed in a particular order, these steps do not necessarily need to be performed in the order illustrated or discussed. The various exemplary methods described and/or illustrated herein may also omit one or more of the steps described or illustrated herein or include additional steps in addition to those disclosed.

The preceding description has been provided to enable others skilled in the art to best utilize various aspects of the exemplary embodiments disclosed herein. This exemplary description is not intended to be exhaustive or to be limited to any precise form disclosed. Many modifications and variations are possible without departing from the spirit and scope of the present disclosure. The embodiments disclosed herein should be considered in all respects illustrative and not restrictive. Reference should be made to the appended claims and their equivalents in determining the scope of the present disclosure.

Unless otherwise noted, the terms "connected to" and "coupled to" (and their derivatives), as used in the specification and claims, are to be construed as permitting both direct and indirect (i.e., via other elements or components) connection. In addition, the terms "a" or "an," as used in the specification and claims, are to be construed as meaning "at least one of." Finally, for ease of use, the terms "including" and "having" (and their derivatives), as used in the specification and claims, are interchangeable with and have the same meaning as the word "comprising."

What is claimed is:

1. An apparatus comprising:
   a line source configured to produce a line of light;
   a scanning device configured to scan the line of light across a scanning field in a scanning direction, the scanning field comprising a receiving portion configured to receive an eye of a user;
   a reflector positioned within the scanning field such that:
      during a primary period of a scan by the scanning device, the line of light scans the receiving portion in a primary direction; and
      during a secondary period of the scan, the reflector reflects the line of light such that a reflection of the line of light scans the receiving portion in a secondary direction; and
   a photodetector positioned to receive:
      an initial reflection produced by the line of light during the primary period of the scan; and
      a subsequent reflection produced by the reflection of the line of light during the secondary period of the scan.

2. The apparatus of claim 1, further comprising a control device communicatively coupled to the line source, the scanning device, and the photodetector, that:
   directs the scanning device to scan the line of light across the scanning field in the scanning direction; and
   detects, via the photodetector, the initial reflection and the subsequent reflection; and
   identifies a location on the eye based on at least one of the initial reflection and the subsequent reflection.

3. The apparatus of claim 2, wherein the control device:
   detects the initial reflection by determining a time of a primary peak in a signal produced by the photodetector during the primary period; and
   detects the subsequent reflection by determining a time of a secondary peak in the signal produced by the photodetector during the secondary period.

4. The apparatus of claim 2, wherein the control device identifies the location on the eye by determining a primary normal angle associated with a primary portion of the eye that produced the initial reflection based on:
   a position of a point of rotation associated with the scanning device;
   an angle of a projection of the line of light from the point of rotation at a time of detection of the initial reflection; and
   a position of the photodetector relative to the point of rotation.

5. The apparatus of claim 2, wherein the control device further identifies a secondary location on the eye by:

identifying an apparent position of an apparent point of rotation associated with the reflection of the line of light; and determining a primary normal angle associated with a secondary portion of the eye that produced the subsequent reflection based on:
   the apparent position of the apparent point of rotation associated with the reflection of the line of light; and
   an apparent angle of an apparent projection of the reflection of the line of light from the apparent point of rotation at a time of detection of the subsequent reflection; and
   an apparent position of the photodetector relative to the apparent point of rotation.

6. The apparatus of claim 5, wherein the control device further tracks a motion of the eye based on at least one of the location on the eye and the secondary location on the eye.

7. The apparatus of claim 1, wherein the line of light is oriented in a primary orientation relative to the primary direction and the reflection of the line of light is oriented in a secondary orientation relative to the primary direction.

8. The apparatus of claim 7, wherein the primary orientation is orthogonal in a common plane to the secondary orientation.

9. The apparatus of claim 1, wherein the photodetector comprises an array of photosensitive elements.

10. The apparatus of claim 9, wherein the array of photosensitive elements comprises at least four photosensitive elements.

11. The apparatus of claim 1, wherein:
   the line source comprises a laser fan source; and
   the line of light comprises an edge of a laser fan generated by the laser fan source.

12. The apparatus of claim 1, wherein the line source, the scanning device, the reflector, and the photodetector are included in a head-mounted display worn by a user.

13. The apparatus of claim 12, wherein the head-mounted display comprises a waveguide display.

14. A method comprising:
   directing a scanning device to scan a line of light, produced by a line source, across a scanning field in a scanning direction, the scanning field comprising a receiving portion configured to receive an eye of a user, wherein:
      during a primary period of the scan, the line of light scans the receiving portion in a primary direction; and
      during a secondary period of the scan, a reflector positioned within the scanning field reflects the line of light such that a reflection of the line of light scans the receiving portion in a secondary direction;
   detecting, via a photodetector:
      an initial reflection produced by the line of light during the primary period; and
      a subsequent reflection produced by the reflection of the line of light during the secondary period; and
   identifying a location on the eye based on at least one of the initial reflection and the subsequent reflection.

15. The method of claim 14, further comprising:
   directing the scanning device to execute a return scan of the line of light across the scanning field in a return direction, wherein:
      during a primary return period of the return scan, the reflector reflects the line of light such that an additional reflection of the line of light scans across the receiving portion in the primary direction; and
      during a secondary return period of the return scan, the line of light scans across the receiving portion in the secondary direction; and
   detecting, via the photodetector, an additional initial reflection produced by the additional reflection of the line of light during the primary return period of the return scan and an additional subsequent reflection produced by the line of light during the secondary return period of the return scan.

16. The method of claim 14, wherein:
   detecting the initial reflection comprises determining a time of a primary peak in a signal produced by the photodetector during the primary period; and
   detecting the subsequent reflection comprises determining a time of a secondary peak in the signal produced by the photodetector during the secondary period.

17. The method of claim 14, wherein identifying the location on the eye comprises determining a primary normal angle associated with a primary portion of the eye that produced the initial reflection based on:
   a position of a point of rotation associated with the scanning device;
   an angle of a projection of the line of light from the point of rotation at a time of detection of the initial reflection; and
   a position of the photodetector relative to a position of a point of rotation associated with the scanning device.

18. The method of claim 17, further comprising identifying a secondary location on the eye, the identifying of the secondary location on the eye comprising:
   identifying an apparent position of an apparent point of rotation associated with the reflection of the line of light; and
   determining a primary normal angle associated with a secondary portion of the eye that produced the initial reflection based on:
      the apparent position of the apparent point of rotation associated with the reflection of the line of light; and
      an angle of a projection of the reflection of the line of light from the apparent point of rotation at a time of detection of the subsequent reflection; and
      a position of the photodetector relative to the apparent point of rotation.

19. The method of claim 18, further comprising tracking a motion of the eye based on at least one of the location on the eye and the secondary location on the eye.

20. A non-transitory computer-readable medium comprising computer-readable instructions that, when executed by at least one processor of a computing system, cause the computing system to:
   direct a scanning device to scan a line of light, produced by a line source, across a scanning field in a scanning direction, the scanning field comprising a receiving portion configured to receive an eye of a user, wherein:
      during a primary period of the scan, the line of light scans the receiving portion in a primary direction; and
      during a secondary period of the scan, a reflector positioned within the scanning field reflects the line of light such that a reflection of the line of light scans the receiving portion in a secondary direction;
   detect, via a photodetector:
      an initial reflection produced by the line of light during the primary period; and
      a subsequent reflection produced by the reflection of the line of light during the secondary period; and identify a location on the eye based on at least one of the initial reflection and the subsequent reflection.

* * * * *